(12) United States Patent
Butters et al.

(10) Patent No.: US 11,103,721 B2
(45) Date of Patent: Aug. 31, 2021

(54) CONTROLLER AND FLEXIBLE COILS FOR ADMINISTERING THERAPY, SUCH AS FOR CANCER THERAPY

(71) Applicant: Nativis, Inc., Seattle, WA (US)

(72) Inventors: John T. Butters, Langley, WA (US);
Bennett M. Butters, Lacey, WA (US);
Mike Ammerman, San Clemente, CA (US); Scott Conway, Yorba Linda, CA (US); Robert Fish, Rancho Cucamonga, CA (US); Larry Hood, Irvine, CA (US); Jared Nathanson, Mission Viejo, CA (US); Kevin Oberkramer, Placentia, CA (US); Kathryn Kukulka, Laguna Beach, CA (US); Andrew March, Lake Forest, CA (US)

(73) Assignee: Natives, Inc., Seattle, WA (US)

( * ) Notice: Subject to any disclaimer, the term of this patent is extended or adjusted under 35 U.S.C. 154(b) by 0 days.

(21) Appl. No.: 16/032,024

(22) Filed: Jul. 10, 2018

(65) Prior Publication Data

US 2019/0184188 A1    Jun. 20, 2019

Related U.S. Application Data

(62) Division of application No. 14/774,688, filed as application No. PCT/US2014/030018 on Mar. 15, 2014, now Pat. No. 10,046,172.

(Continued)

(51) Int. Cl.
*A61N 2/02* (2006.01)
*A61N 2/00* (2006.01)
(Continued)

(52) U.S. Cl.
CPC ............... *A61N 2/02* (2013.01); *A61N 2/002* (2013.01); *A61N 2/004* (2013.01); *G01N 37/005* (2013.01);
(Continued)

(58) Field of Classification Search
CPC .................................................. A61N 2/00–12
See application file for complete search history.

(56) References Cited

U.S. PATENT DOCUMENTS

| 4,031,462 A | 6/1977 | Bouvier et al. |
| 4,095,168 A | 6/1978 | Hlavka |

(Continued)

FOREIGN PATENT DOCUMENTS

| AU | 2003231978 | 2/2005 |
| AU | 2003230950 | 11/2006 |

(Continued)

OTHER PUBLICATIONS

United States Patent and Trademark Office International Searching Authority; International Search Report and Written Opinion; PCT Application No. PCT/US05/26629; Applicant: Nativis, Inc.; dated Aug. 7, 2008; 8 pages.

(Continued)

*Primary Examiner* — Thaddeus B Cox
(74) *Attorney, Agent, or Firm* — Perkins Coie LLP

(57) ABSTRACT

Disclosed herein are systems and methods for providing a portable magnetic field therapy system for treatment of diseases and adverse health conditions, such as cancer.

17 Claims, 18 Drawing Sheets

Related U.S. Application Data

(60) Provisional application No. 61/792,547, filed on Mar. 15, 2013.

(51) Int. Cl.
  *G01N 37/00* (2006.01)
  *A61M 37/00* (2006.01)

(52) U.S. Cl.
  CPC ................ *A61B 2562/0223* (2013.01); *A61M 2037/0007* (2013.01); *A61M 2250/00* (2013.01)

(56) References Cited

U.S. PATENT DOCUMENTS

| | | |
|---|---|---|
| 4,365,303 A | 12/1982 | Hannah et al. |
| 4,369,226 A | 1/1983 | Rembaum et al. |
| 4,548,208 A * | 10/1985 | Niemi ................ A61N 2/02 600/14 |
| 4,682,027 A | 7/1987 | Wells |
| 4,692,685 A | 9/1987 | Blaze |
| 4,751,515 A | 6/1988 | Corum |
| 4,822,169 A | 4/1989 | Distl et al. |
| 5,113,136 A | 5/1992 | Hayashi et al. |
| 5,254,950 A | 10/1993 | Fan et al. |
| 5,305,751 A | 4/1994 | Chopp et al. |
| 5,339,811 A | 8/1994 | Ohta et al. |
| 5,343,147 A | 8/1994 | Sager et al. |
| 5,446,681 A | 8/1995 | Gethner et al. |
| 5,458,142 A | 10/1995 | Farmer |
| 5,465,049 A | 11/1995 | Matsuura et al. |
| 5,506,500 A | 4/1996 | Krause et al. |
| 5,508,203 A | 4/1996 | Fuller |
| 5,541,413 A | 7/1996 | Pearson et al. |
| 5,574,369 A | 11/1996 | Hibbs |
| 5,583,432 A | 12/1996 | Barnes |
| 5,656,937 A | 8/1997 | Cantor |
| 5,696,691 A | 12/1997 | Schlosser et al. |
| 5,734,353 A | 3/1998 | Van Voorhies |
| 5,752,514 A | 5/1998 | Okamura et al. |
| 5,789,961 A | 8/1998 | Bulsara et al. |
| 5,944,782 A | 8/1999 | Noble et al. |
| 5,952,978 A | 9/1999 | Van Voorhies |
| 5,955,400 A | 9/1999 | Yokosawa et al. |
| 5,959,548 A | 9/1999 | Smith |
| 6,020,782 A | 2/2000 | Albert et al. |
| 6,028,558 A | 2/2000 | Van Voorhies |
| 6,084,242 A | 7/2000 | Brown et al. |
| 6,084,399 A | 7/2000 | Nagaishi et al. |
| 6,133,734 A | 10/2000 | McKeon |
| 6,136,541 A | 10/2000 | Gulati |
| 6,142,681 A | 11/2000 | Gulati |
| 6,150,812 A | 11/2000 | Pinsky et al. |
| 6,159,444 A | 12/2000 | Schlenga et al. |
| 6,196,057 B1 | 3/2001 | Discenzo |
| 6,201,821 B1 | 3/2001 | Zhu et al. |
| 6,204,821 B1 | 3/2001 | Van Voorhies |
| 6,285,249 B1 | 9/2001 | Bulsara et al. |
| 6,294,911 B1 | 9/2001 | Shimazawa et al. |
| 6,320,369 B1 | 11/2001 | Hidaka et al. |
| 6,323,632 B1 | 11/2001 | Husher et al. |
| 6,411,108 B1 | 6/2002 | Douglas et al. |
| 6,433,543 B1 | 8/2002 | Shahinpoor et al. |
| 6,516,281 B1 | 2/2003 | Wellstood et al. |
| 6,541,978 B1 | 4/2003 | Benveniste et al. |
| 6,586,931 B2 | 7/2003 | Taicher |
| 6,665,553 B2 | 12/2003 | Kandori et al. |
| 6,724,188 B2 | 4/2004 | Butters et al. |
| 6,760,674 B2 | 7/2004 | Bombard |
| 6,815,949 B2 | 11/2004 | Kandori et al. |
| 6,885,192 B2 | 4/2005 | Clarke et al. |
| 6,952,652 B2 | 10/2005 | Butters |
| 6,995,558 B2 | 2/2006 | Butters et al. |
| 7,081,747 B2 | 7/2006 | Butters et al. |
| 7,130,692 B2 | 10/2006 | Brighton et al. |
| 7,280,078 B2 | 10/2007 | Salsman et al. |
| 7,412,340 B2 | 8/2008 | Butters |
| 7,573,264 B2 | 8/2009 | Xu et al. |
| 7,575,934 B2 | 8/2009 | Atwood |
| 7,687,269 B2 | 3/2010 | Kautz et al. |
| 7,993,581 B2 | 8/2011 | Seki et al. |
| 8,760,159 B2 | 6/2014 | Tuchman |
| 9,417,257 B2 | 8/2016 | Butters et al. |
| 10,046,172 B2 | 8/2018 | Butters et al. |
| 2002/0158631 A1 | 10/2002 | Kandori et al. |
| 2003/0016010 A1 | 1/2003 | Kandori et al. |
| 2003/0184289 A1 | 10/2003 | Butters et al. |
| 2004/0027125 A1 | 2/2004 | Clarke et al. |
| 2004/0174154 A1 | 9/2004 | Butters |
| 2004/0181115 A1 * | 9/2004 | Sandyk ................ A61N 1/40 600/9 |
| 2004/0183530 A1 | 9/2004 | Butters et al. |
| 2004/0222789 A1 | 11/2004 | Pinsky et al. |
| 2005/0030016 A1 | 2/2005 | Butters et al. |
| 2005/0176391 A1 | 8/2005 | Butters |
| 2006/0030896 A1 | 2/2006 | Simon et al. |
| 2006/0158183 A1 | 7/2006 | Butters et al. |
| 2007/0205767 A1 | 9/2007 | Xu et al. |
| 2007/0210790 A1 | 9/2007 | Butters et al. |
| 2007/0231872 A1 | 10/2007 | Butters et al. |
| 2008/0011977 A1 | 1/2008 | Atwood |
| 2008/0106261 A1 | 5/2008 | Romalis et al. |
| 2008/0306325 A1 * | 12/2008 | Burnett ................ A61N 2/02 600/13 |
| 2009/0156659 A1 | 6/2009 | Butters et al. |
| 2010/0228075 A1 * | 9/2010 | Lu ................ A61N 2/006 600/13 |
| 2011/0279115 A1 | 11/2011 | Tuchman |
| 2012/0089201 A1 | 4/2012 | Pilla |
| 2012/0113423 A1 | 5/2012 | Groswasser |
| 2012/0130149 A1 | 5/2012 | Diament et al. |
| 2012/0253101 A1 | 10/2012 | Wang et al. |
| 2013/0041201 A1 | 2/2013 | Butters et al. |
| 2013/0121879 A1 | 5/2013 | Kawabata et al. |
| 2013/0165734 A1 | 6/2013 | Butters |
| 2014/0303425 A1 * | 10/2014 | Pilla ................ A61B 5/0488 600/14 |
| 2017/0067969 A1 | 3/2017 | Butters |
| 2019/0143135 A1 | 5/2019 | Butters |

FOREIGN PATENT DOCUMENTS

| | | |
|---|---|---|
| AU | 2004280998 | 4/2008 |
| AU | 2005269345 | 8/2010 |
| AU | 2011201847 | 9/2013 |
| AU | 2013290020 | 8/2017 |
| BR | PI0307210 | 12/2004 |
| BR | PI0415235 | 12/2006 |
| BR | PI0512678 | 4/2008 |
| BR | PI0513910 | 5/2008 |
| CA | 2460794 | 2/2005 |
| CA | 2574616 | 7/2006 |
| CA | 2538988 | 2/2011 |
| CA | 2684009 | 2/2011 |
| CA | 2473142 | 4/2011 |
| CA | 2573350 | 5/2014 |
| CN | 200991511 Y | 12/2007 |
| CN | ZL200480029490.2 | 5/2010 |
| CN | 102335483 | 2/2012 |
| CN | ZL200580025199.2 | 5/2012 |
| CN | 1633603 | 6/2012 |
| CN | 104620123 | 5/2015 |
| CN | 105339041 | 2/2016 |
| DE | 1815674 | 7/1969 |
| EP | 0060392 | 9/1982 |
| EP | 1792179 | 6/2007 |
| FR | 2783605 | 3/2000 |
| HK | 1104855 A | 1/2008 |
| IN | 229893 | 2/2009 |
| IN | 237823 | 1/2010 |
| IN | 252124 | 4/2012 |
| IN | 195/DELNP/2015 | 8/2016 |
| JP | 2004318323 | 11/2004 |

(56) References Cited

FOREIGN PATENT DOCUMENTS

| | | |
|---|---|---|
| JP | 2006127648 | 5/2006 |
| JP | 2007065953 | 3/2007 |
| JP | 2008508523 | 3/2008 |
| JP | 4425639 | 12/2009 |
| JP | 4425922 | 3/2010 |
| JP | 5624708 | 10/2014 |
| WO | 8606493 | 11/1986 |
| WO | 8702981 | 5/1987 |
| WO | 9113611 | 9/1991 |
| WO | 9114181 | 9/1991 |
| WO | 9417406 | 8/1994 |
| WO | 9954731 | 10/1999 |
| WO | 2000001412 | 1/2000 |
| WO | 2000017637 | 3/2000 |
| WO | 2000017638 | 3/2000 |
| WO | 2003083429 | 10/2003 |
| WO | 2003083439 | 10/2003 |
| WO | 2003102566 | 12/2003 |
| WO | 2005015213 | 2/2005 |
| WO | 2005036131 | 4/2005 |
| WO | 2006060653 | 12/2005 |
| WO | 2006015038 | 2/2006 |
| WO | 2005118858 | 6/2006 |
| WO | 2006073491 | 7/2006 |
| WO | 2007138598 | 12/2007 |
| WO | 2008008257 | 1/2008 |
| WO | 2008023840 | 2/2008 |
| WO | 2008063654 | 5/2008 |
| WO | 2010117349 | 10/2010 |
| WO | 2011075692 | 6/2011 |
| WO | 2014011940 | 1/2014 |
| WO | 2014145284 | 9/2014 |

OTHER PUBLICATIONS

United States Patent and Trademark Office International Searching Authority; International Search Report; PCT Application No. PCT/US03/009544; Applicant: Wavbank, Inc.; dated Sep. 9, 2003; 3 pages.

United States Patent and Trademark Office International Searching Authority; International Search Report; PCT Application No. PCT/US03/011834; Applicant: Wavbank, Inc.; dated Oct. 9, 2003; 4 pages.

United States Patent and Trademark Office International Searching Authority; International Search Report; PCT Application No. PCT/US04/033383; Applicant: Wavbank, Inc.; dated May 27, 2005; 4 pages.

Aissa et al., "Transatlantic Transfer of Digitized Antigen Signal by Telephone Link", Digi Bio-FASEB 97, Abstract only, http://digibio.com/cgi-bin/node.pl?Ig=us&nd=n4_3 (1997).

Aissa et al., "Electronic transmission of the cholinergic signal", FASEB Journal, A683, Poster 3964, 1995, Abstract only.

Aissa, et al., "Transfer of molecular signals via electronic circuitry", FASEB Journal, A602, Poster #3489, 1993, Abstract only.

Aissa, et al., "Molecular signaling at high dilution or by means of electronic circuitry", Journal of Immunology, 146A, 1994, Abstract only.

Atkins, P. W. Ed—Atkins P. W.: "Physical Chemistry, Magnetic resonance", Jan. 1, 1990, Physical Chemistry, Oxford University Press, Oxford, pp. 535-563.

Atkins, P.W., "Rotational and Vibrational Spectra," Physical Chemistry, Oxford University Press, Oxford, UK, 1990, pp. 458-497.

Balog, A. et al., Total Synthesis of ( − )-Epothilone A**, Angewandte Chemie International Edition in English, vol. 35, Issue 23-24, Dec. 1996, pp. 2801-2803.

Bendat, J. S. et al., Engineering Applications of Correlation and Spectral Analysis, 2nd edition. Wiley-Interscience, 1993, Abstract only.

Benveniste et al., "A Simple and Fast Method for in Vivo Demonstration of Electromagnetic Molecular Signaling (EMS) via High Dilution or Computer Recording", FASEB Journal, vol. 13, p. A163, 1999, Abstract only.

Benveniste et al., "Digital Biology: Specificity of the Digitized Molecular Signal", FASEB Journal, vol. 12, p. A412, 1998, Abstract only.

Benveniste et al., "The Molecular Signal is not Functional in the Absence of "Informed" Water", FASEB Journal, vol. 13, p. A163, 1999, Abstract only, <http://digibio.com/cgi-bin/node.pl?Ig=us&nd=n4_11>.

Benveniste et al., "Digital Recording Transmission of the Cholinergic Signal", DigiBio-FASEB 96, 1996, Abstract only, <http://digibio.com/cgi-bin/node.pl?Ig=us&nd=n4_ 4>.

Benveniste, J., "From 'Water Memory' effects to 'Digital Biology'", Understanding Digital Biology, 4 pages, Jun. 14, 1998, <http://www.digibio.com/cgi-bin/node.pl?nd=n3>, <.

Benveniste, J., "Molecular Signaling, What Is So Unacceptable for Ultra-Orthodox Scientists?", 2 pages, 2003, <http://www.digibio.com/cgi-bin/node.pl?nd=n5>.

Benveniste et al., "Specific Remote Detection of Bacteria Using an Electromagnetic/Digital Procedure", FASEB Journal, vol. 13, p. A852, 1999, Abstract only, <http://digibio.com/cgi-bin/node.pl?Ig=us&nd=n4.sub.--12>.

Benveniste, J., et al., "Transfer of the molecular signal by electronic amplification", FASEB Journal, A398, Poster #2304, 1994, Abstract only.

Binhi, V., "An Analytical Survey of Theoretical Studies in the Area of Magnetoreception", 11 pages, 1999, <http://www.biomag.info/survey.htm>.

Brault, J., et al., "The Analysis and Restoration of Astronomical Data via the Fast Fourier Transform", 1971, Astronomy and Astrophysics, 11(2):169-189.

Brigham, E., "The Fast Fourier Transform and Applications", Prentice Hall, 1988, pp. 131-145.

Bruno A. C., "Design of a SQUID array as a discrete spacial filter", Superconductor Science and Technology, vol. 17, NR: 7, pp. 908-915 (2004).

Chapeau-Blondeau, F., "Input-output gains for signal in noise in stochastic resonance", Physics Letters A, vol. 232, Jul. 21, 1997, Elsevier Science B.V., pp. 41-48.

Chapeau-Blondeau, F., "Periodic and Aperiodic Stochastic Resonance with Output Signal-to-Noise Ratio Exceeding That At the Input", International Journal of Bifurcation and Chaos, 9(1):267-272, 1999.

Chemla et al., "Ultrasensitive magnetic biosensor for homogeneous immunoassay", PNAS, 97(26): 14268-14272, 2000.

Cooley, J. et al., "An Algorithm for the Machine Calculation of Complex Fourier Series", Mathematics of Computation, American Mathematical Society, Providence, Rhode Island, 19(90):297-301, 1965.

Crut, A. et al., "Detection of single DNA molecules by multicolor quantum-dot end-labeling", Nucleic Acids Research, vol. 33, No. 11, e98, 2005, pp. 1-9.

DigiBio S.A., Experimental models, From "Water Memory" effects to "Digital Biology", 2003, <http://digibio.com/cgi-bin/node.pl?nd=n7>.

"Direct Nanoscale Conversion of Bio-Molecular Signals Into Electronic Information" DARPA Defense Sciences Office, 2 pages, 2003, <http://www.darpa.mil/dso/thrust/biosci/moldice.htm>.

Dubertret, B. et al., "In Vivo Imaging of Quantum Dots Encapsulated in Phospholipid Micelles", Science, vol. 298, Nov. 29, 2002, pp. 1759-1762.

Duhamel, P., et al., "Split radix' FFT algorithm", Electronics Letters, The Institution of Electrical Engineers, 20(1):14-16, 1984.

"Engineered Bio-Molecular Nano-Devices/Systems (MOLDICE)" DARPA Defense Sciences Office, 1 page, 2004, <http://www.darpa.mil/dso/thrust/biosci/moldice.htm>.

The First International Workshop on TFF; What is Biophysies Behind?, Abstract Booklet, Jun. 15, 1996, 18 pages, <http://www.biophysics.nl/idras.htm>.

Gao, X. et al. "In vivo molecular and cellular imaging with quantum dots", Current Opinion in Biotechnology, vol. 16, 2005, pp. 63-72.

Glanz, J., "Sharpening the Senses with Neural 'Noise'", Science, 277(5333), 2 pages, 1997, <http://complex.gmu.edu/neural/papers/others/science97.sub.--noise.html>.

(56) References Cited

OTHER PUBLICATIONS

Gorgun, S., "Studies on the Interaction Between Electromagnetic Fields and Living Matter Neoplastic Cellular Culture", I(2):22 pages, 1998, <http://bodyvibes.com/study1.htm>.
Grabarek et al., "Zero-Length Crosslinking Procedure with the Use of Active Esters", Journal of Analytical Biochemistry, vol. 185, 1990, pp. 131-135.
Haller et al., "Low Tc SQUID Measurement System for Magnetic Relaxation Immunoassays in Unshielded Environment", IEEE Transactions on Applied Superconductivity, vol. 11, Mar. 2001, pp. 1371-1374.
Han et al., "Quantum-dot-tagged microbeads for multiplexed optical coding of biomolecules", Nature Biotechnology, vol. 19, Jul. 2001, pp. 631-635.
Hatanaka, S. et al.: "Direct immobilization of fluorescent dyes onto ferrite nanoparticles during their synthesis from aqueous solution", Journal of Applied Physics, American Institute of Physics. New York, US, vol. 93, No. 10, May 15, 2003, pp. 7569-7570.
Hendrickson, W., "Protein-DNA Interactions Studied by the Gel Electrophoresis-DNA Binding Assay", BioTechniques, vol. 3, May/Jun. 1985, pp. 198-207.
Hibbs et al., "Signal Enhancement in a r.f. SQUID using Stochastic Resonance", IL Nuovo Cimento, 11, 1995, pp. 811-817.
Hoffman, F., "An Introduction to Fourier Theory", 10 pages, 2004, <http://aurora.phys.utk.edu/-forrest/papers/fourier/index.html>.
Ingram, D.J.E., "Spectroscopy at Radio and Microwave Frequencies," New York Plenum Press, Butterworths, London, UK, 1967, pp. 1-16.
Kaufman, I. et al., "Zero-dispersion stochastic resonance in a model for a superconducting quantum interference device", Physical Review E, 57(1 ):78-87, The American Physical Society, 1998.
Lee, J. C. et al., In Vitro Reconstitution of Calf Brain Microtubules: Effects of Solution Variables, Biochemistry, vol. 16, No. 8, Apr. 19, 1977, pp. 1754-1764.
Maehle et al., "The emergence of the drug receptor theory", Nat. Rev. Drug Disc., vol. 1, No. 8, pp. 637-641, 2002.
Magana, D. J. et al., "Switching-on Superparamagnetism in MN/CdSE Quantum Dots", Journal of American Chemical Society, vol. 128, No. 9, 2006, pp. 2931-2939.
"MDA-MB-4355 (ATCC HTB 129) Product Sheet", American Type Culture Collection, 3 pages, 2014, <http://www.atcc.org/Products/All/HTB-129.aspx#documentation>.
Melle, S. et al., "Structure and dynamics of magnetorheological fluids in rotating magnetic fields", The American Physical Society: Physical Review E, vol. 61., No. 4, Apr. 2000, pp. 4111-4117.
Moini, H. et al., "Protein Binding of Procyanidins: Studies Using Polyacrylamide Gel Electrophoresis and French Maritime Pine Bark Extract", Methods in Enzymology, vol. 335, 2001, pp. 333-337.
Morozov et al., "Active bead-linked immunoassay on protein microarrays", Analytica Chimica Acta, Elsevier, Amsterdam, NL, vol. 564, No. 1, Mar. 30, 2006, pp. 40-52.
Mulder et al., "Improved HSQC experiments for the observation of exchange broadened signals", J. Biomol. NMR, vol. 8, No. 2, 1996, pp. 223-228.
Mulvaney. S. et al., "Incorporating fluorescent dyes and quantum dots into magnetic microbeads for immunoassays", BioTechniques, vol. 36, Apr. 2004, pp. 602-609.
Neuhauser, R., "Hydrogenlike Rydberg Electrons Orbiting Molecular Clusters", Physical Review Letters, The American Physical Society, 80(23), 1998, pp. 5089-5092.
Nokazi, D., et al., "Effects of Colored Noise on Stochastic Resonance in Sensory Neurons", Physical Review Letters, The American Physical Society, vol. 82, No. 11, Mar. 15, 1999, pp. 2402-2405.
Nuzzo, R. et al., "Adsorption of Bifunctional Organic Disulfides on Gold Surfaces", Journal of American Chemical Society, vol. 105, No. 13, 1983, pp. 4481-4483.
Olivos, H. et al., "Quantum Dots as a Visual Aid for Screening Bead-Bound Combinatorial Libraries", ChemBioChem, vol. 4, 2003, pp. 1242-1245.
Oppenheim et al., "Digital Signal Processing", Prentice-Hall, ISBN 0-13-214635-5, Ch. 3, The Discrete Fourier Transform, 1975, pp. 87-121.
Proakis, J.G., et al., "Advanced digital signaling processing", Maxwell MacMillan, Ch. 1.3, Sampling of Signals in Time and Frequency, 1992, pp. 31-56.
Shelanski, M. L. et al., Microtubule Assembly in the Absence of Added Nucleotides, Proceeding of the National Academy of Sciences U.S.A., vol. 70, No. 3, Mar. 1973, pp. 765-768.
Soma, R., "Noise Outperforms White Noise in Sensitizing Baroreflex Function in the Human Brain", The American Physical Society, Physical Review Letters, 91(7), 2003, 4 pages.
Staros, J. et al., "Enhancement by N-Hydroxysulfosuccinimide of Water-Soluble Carbodiimide-Mediated Coupling Reactions", Analytical Biochemistry, vol. 156, 1986, pp. 220-222.
Temperton, C. Implementation of a Self-Sorting In-Place Prime Factor FFT Algorithm, Journal of Computation Physics, vol. 58, 1985, p. 283.
Thomas et al., "Direct transmission to cells of a molecular signal via an electronic device", FASEB Journal, A227, Poster # 1320, 1995, Abstract only.
Thomas et al., "Modulation of Human Neutrophil Activation by "Electronic" Phorbol Myristate Acetate (PMA)", DigiBio, 1996, Abstract only, <http://www.digibio.com/cgibin/node.pl?Ig=us&nd=n4.sub._5>.
Thomas, Y. et al., "Activation of human neurophils by electronically transmitted phorbol-myristate acetate", Medical Hypotheses, 2000, 54(1 ), pp. 33-39.
Turin, L., Department of Anatomy and Developmental Biology University College London, "A spectroscopic mechanism for primary olfactory reception", Chemical Senses, vol. 21 (6), 1996, pp. 773-791.
United States Patent and Trademark Office International Searching Authority, International Preliminary Report on Patentability; International Patent Application No. PCT/US2009/002184; Applicant: Nativis, Inc.; dated Oct. 11, 2011; 8 pages.
United States Patent and Trademark Office International Searching Authority, International Search Report; International Patent Application No. PCT/US2009/002184; Applicant: Nativis, Inc.; dated Jun. 4, 2009; 2 pages.
United States Patent and Trademark Office International Searching Authority, Written Opinion of the International Searching Authority; International Patent Application No. PCT/US2009/002184; Applicant: Nativis, Inc.; dated Jun. 4, 2009; 7 pages.
Weaver, J., et al., "The response of living cells to very weak electric fields: the thermal noise limit.", Science, 247(4941):459-462, 1990, Abstract only, <http://www.ncbi.nlm.nih.gov/entrezlgueey.fcgi?db=PubMed&cmd=Retrieve&_list.sub_uids=2300806&dopt=Citation>.
Wikswo, J. et al., "Magnetic Field of a Nerve Impulse: First Measurements", Science, vol. 208, Apr. 4, 1980, pp. 53-55.
Yi, D. et al. "Silica-Coated Nanocomposites of Magnetic Nanoparticles and Quantum Dots", Journal of American Chemical Society, vol. 127, 2005, pp. 4990-4991.
European Patent Office, Supplemental European Search Report; EP Application No. 13817486.7; Applicant: Nativis, Inc.; dated Dec. 2, 2015; 10 pages.
Hore et al., "Spin-Spin Coupling," Nuclear Magnetic Resonance, Chapter 3, Oxford University Press, 1995, pp. 22-43.
Korean Intellectual Property Office International Searching Authority; International Search Report and Written Opinion; PCT Application No. PCT/US14/030018; Applicant: Nativis, Inc.; dated Sep. 11, 2014; 20 pages.
Blanchard et al.: "High-Resolution Zero-Field NMR J-Spectroscopy of Aromatic Compounds," Journal of the American Chemical Society, vol. 135, No. 9, Feb. 7, 2013, pp. 3607-3612.
Ledbetter et al.: "Near-Zero-Field Nuclear Magnetic Resonance," Physical Review Letters, vol. 107, No. 10, Sep. 1, 2011.
Ledbetter et al.: "Optical Detection of NMR J-spectra at Zero Magnetic Field," Journal of Magnetic Resonance, vol. 199, No. 1, Mar. 28, 2009, pp. 25-29.
Extended European Search Report in Application No. 14762988.5, dated Jul. 18, 2016, 9 pages.

(56) References Cited

OTHER PUBLICATIONS

International Search Report and Written Opinion in Application No. PCT/US13/50165, dated May 27, 2014, 12 pages.

Ulasov et al., "Precision knockdown of EGFR gene expression using radio frequency electromagnetic energy," Journal of Neuro-Oncology, Apr. 22, 2017, vol. 133, Issue 2, pp. 257-264, 8 pages, DOI: 10.1007/511060-017-2440-x.

Pless et al., "Tumor treating fields: concept, evidence and future", Expert Opinion on Investigational Drugs, Epub: May 9, 2011, vol. 20, Issue 8, pp. 1099-1106, 9 pages, DOI: 10.1517/13543784.2011.583236.

Butters et al., "Non-Thermal Radio Frequency Stimulation of Tubulin Polymerization in Vitro: A Potential Therapy for Cancer Treatment," Open Journal of Biophysics, vol. 4, No. 4, Oct. 2014, 23 pages, DOI: 10.4236/ojbiphy.2014.44015.

\* cited by examiner

CONTROLLER AND FLEXIBLE COILS FOR ADMINISTERING THERAPY, SUCH AS FOR CANCER THERAPY

CROSS-REFERENCE TO RELATED APPLICATIONS

This application is a divisional of U.S. application Ser. No. 14/774,688, filed Sep. 10, 2015 (U.S. Pat. No. 10,946, 172), which is a 371 National Phase Application of PCT Application Na PCT/US2014/030018, filed Mar. 15, 2014, which claims priority to U.S. Provisional Application No. 61/792,547, filed Mar. 15, 2013, all of which are incorporated by reference herein in their entireties.

BACKGROUND

Various diseases and adverse health conditions affect people and animals. An example of a disease that affects people and animals is cancer, otherwise known medically as a malignant neoplasm. Cancer includes a broad group of various diseases that involve unregulated cell growth. In 2007, cancer attributed to approximately 13% of all human deaths worldwide, approximately 7.9 million people. Because of its effect on worldwide populations, new treatments for cancer are continually sought and researched.

Traditional treatments for cancer, such as chemotherapy, radiation therapy, and surgery, can be intrusive, can be life altering, and can leave the patient unable to perform routine day-to-day functions. Alternative treatments are desirable.

DETAILED DESCRIPTION

The systems and methods described herein provide example embodiments of a non-intrusive delivery mechanism for treating diseases such as cancer and other adverse health conditions. As discussed above, traditional therapies associated with cancer treatment can leave undesirable side-effects. The Applicant has disclosed, in related patents and patent applications noted herein, systems and methods for detecting and recording molecular signals from chemical, biochemical, or biological molecules or from chemical, biochemical, or biological agents. In some implementations, the recordings represent molecular signals of the chemical, biochemical, or biological molecules or agents used to provide therapy for cancer, ailments or other adverse health conditions. The systems and methods disclosed herein may be configured to deliver the effect of chemical, biochemical, or biologic therapy to a patient without the use of drugs, by generating electromagnetic or magnetic fields that simulate or mimic molecular signals of particular chemicals, biochemical, or biologics. Thus, the systems and methods allow a patient to receive an electronic "prescription" or dosage of electromagnetic or radio frequency energy with, for example, the click of a button. The embodiments of the systems and methods describe a therapy system that is non-invasive, non-thermal, and mobile.

Note, as used herein, the term "drug" is used broadly to define any chemical, biochemical or biologic molecules including proteins, RNA and DNA sequences, etc. As used herein, and described in more detail below, the terms "magnetic field," "electromagnetic field" and similar terms are used interchangeably to represent the presentation of energy to a selected region to address adverse health effects, where the presented energy has a characteristic reflecting that of a specific drug.

Figure 1:
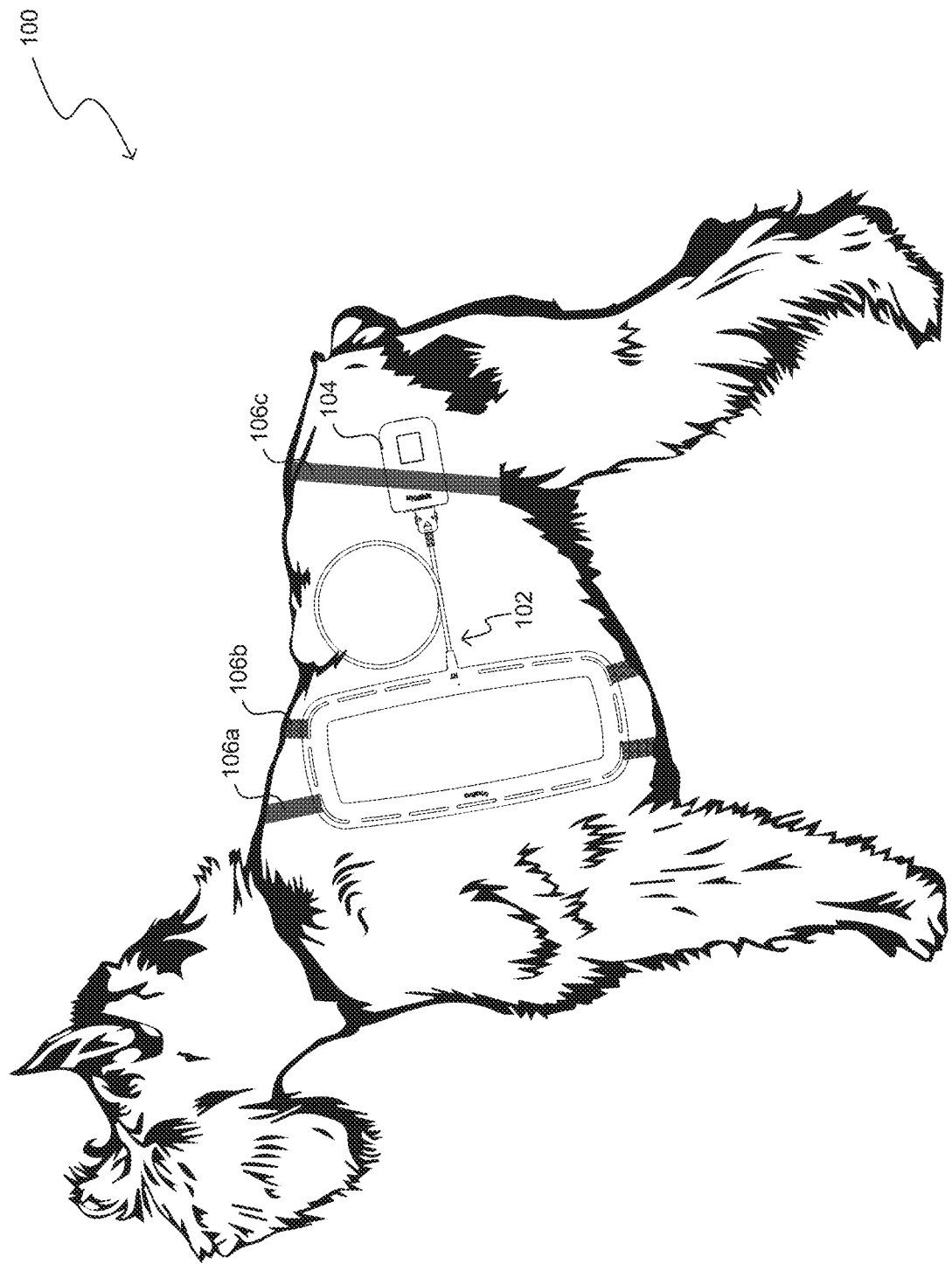
FIG. 1 is a diagram of a therapy system in use on a canine patient.

FIG. 1 illustrates an embodiment of a therapy system 100 for applying magnetic signals to a patient, such as a canine, to provide therapeutic treatment, such as to selectively reduce or inhibit growth of particular types of cells. In some implementations, the therapy system 100 may be used to treat cancer cells by applying electromagnetic or magnetic fields to affected areas. These fields are induced or generated to expose an affected area with signals that mimic signals produced by chemotherapy drugs. Of course, while a canine is shown, and cancer treatment is discussed in general herein, the present system may be used with other patients such as humans, and with many other forms of treating disease or other ailments. The acquisition of the signals produced by chemotherapy drugs is discussed in great detail in patent applications and patents that are co-owned by the assignee of the instant application. These patents and applications include U.S. Pat. Nos. 6,724,188; 6,995,558; 6,952, 652; 7,081,747; 7,412,340; and 7,575,934; and PCT Application No. PCT/US2009/002184, each of which is hereby incorporated by reference in their entirety.

The therapy system 100 may provide various advantages over traditional cancer treatments. For example, the therapy system 100 may be portable and worn or carried by a patient to allow the patient to receive therapy while at home, at work, at school, and during recreation. Furthermore, the therapy system 100 may enable a patient to receive treatments without visiting a health care facility, without incurring extensive recovery time, and possibly without experiencing other traditional side-effects such as: nausea, fatigue, loss of appetite, and the development of infections. The therapy system 100 includes a coil and cable assembly 102 coupled to a controller 104. In accordance with various implementations, the therapy system 100 may be secured to the patient using fasteners 106 (inclusive of 106*a*, 106*b*, and 106*c*), such as tape, elastic bandages, gauze, or the like.

Figure 2:
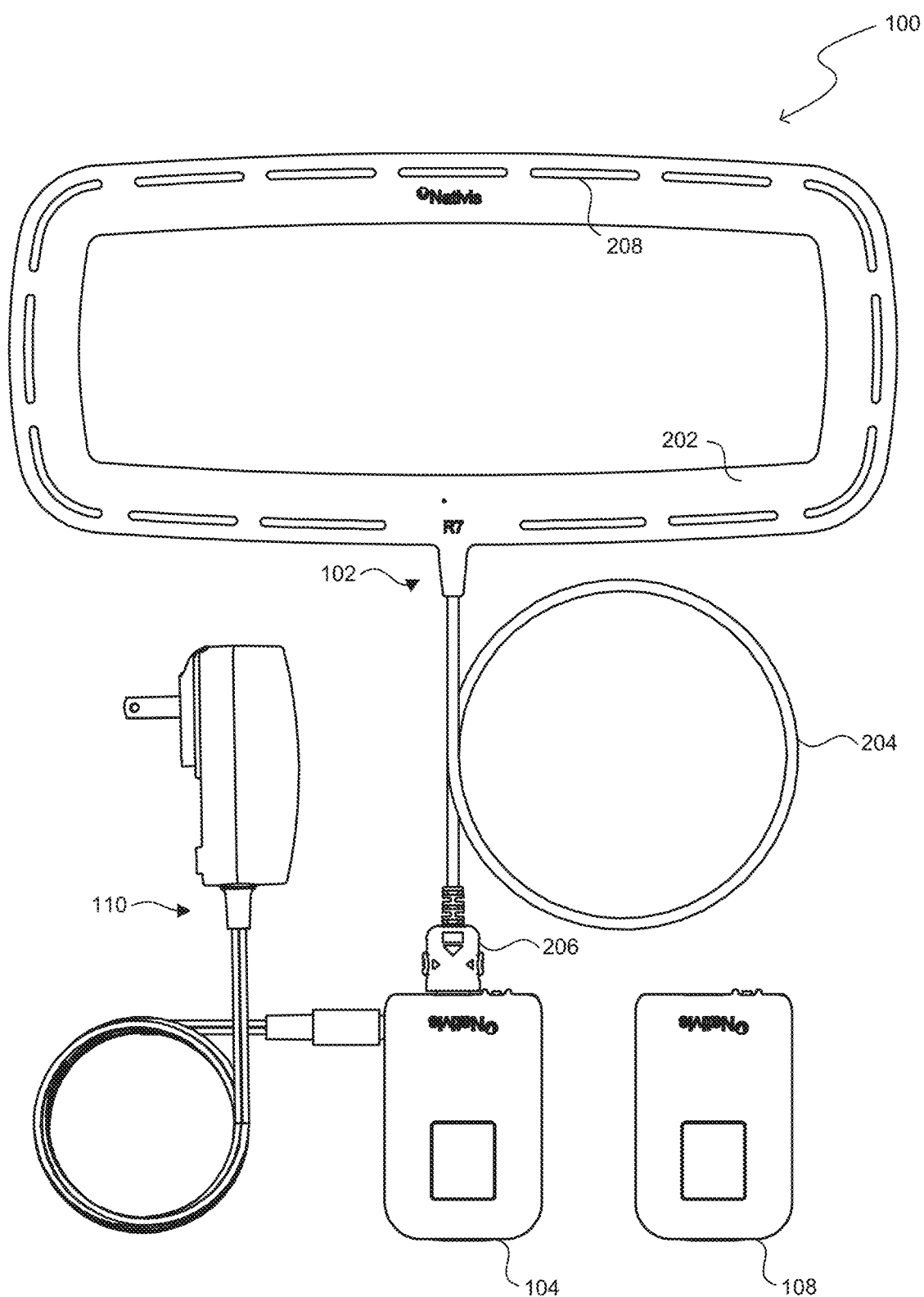
FIG. 2 is another diagram of the therapy system of FIG. 1.

FIG. 2 illustrates the therapy system 100 as it may be provided to a physician or patient. In addition to the coil and cable assembly 102 and the controller 104, when delivered to a customer, the therapy system 100 may also include an additional controller 108 and a battery charging device 110. For various security reasons which are discussed below, each controller may be manufactured so that a housing for the controller cannot be opened easily. The tamper-resistant housing may therefore make it difficult to interchange one battery for another. Therefore, to allow a patient to continuously receive therapy with the therapy system 100, one or more additional controllers 108 may be provided to allow the patient to receive therapy while the controller 104 is charging with the charging device 100. The coil, cable and connector assembly 102 may be disposable, or the system as a whole together with the one or more controllers 104, 108. Thus the coil and cable assembly 102 and/or controller 104, 108 are preferably provided for a single therapeutic session and for one prescription, so that the controller and coil assembly are not to be reused, thereby preventing cross contamination, etc.

Therapy System Coil and Cable Assembly

In FIG. 2, the coil and cable assembly 102 includes an encapsulated coil 202, a cable 204, and a connector 206. The coil 202 includes one or more conductors configured to generate a magnetic or electromagnetic field to mimic drug-simulating signals. As used herein, a drug-simulating signal includes a signal that approximately reproduces magnetic fields that emanate from one or more predetermined chemical, biochemical, and/or biological molecules or agents. The coil 202 may be configured to have various electrical characteristics. Additionally, the coil 202 may be enclosed in a plastic or other composite material to both protect the windings of the coil and to provide a comfortable interface for the wearer. The coils can be flexible and malleable, can have a variety of shapes, can have different sizes or types, and can also include rigid coils. Advantageously, these coils can be externally secured to a patient to provide treatment, as opposed to subcutaneous insertion of the coil into a patient.

Figure 3:
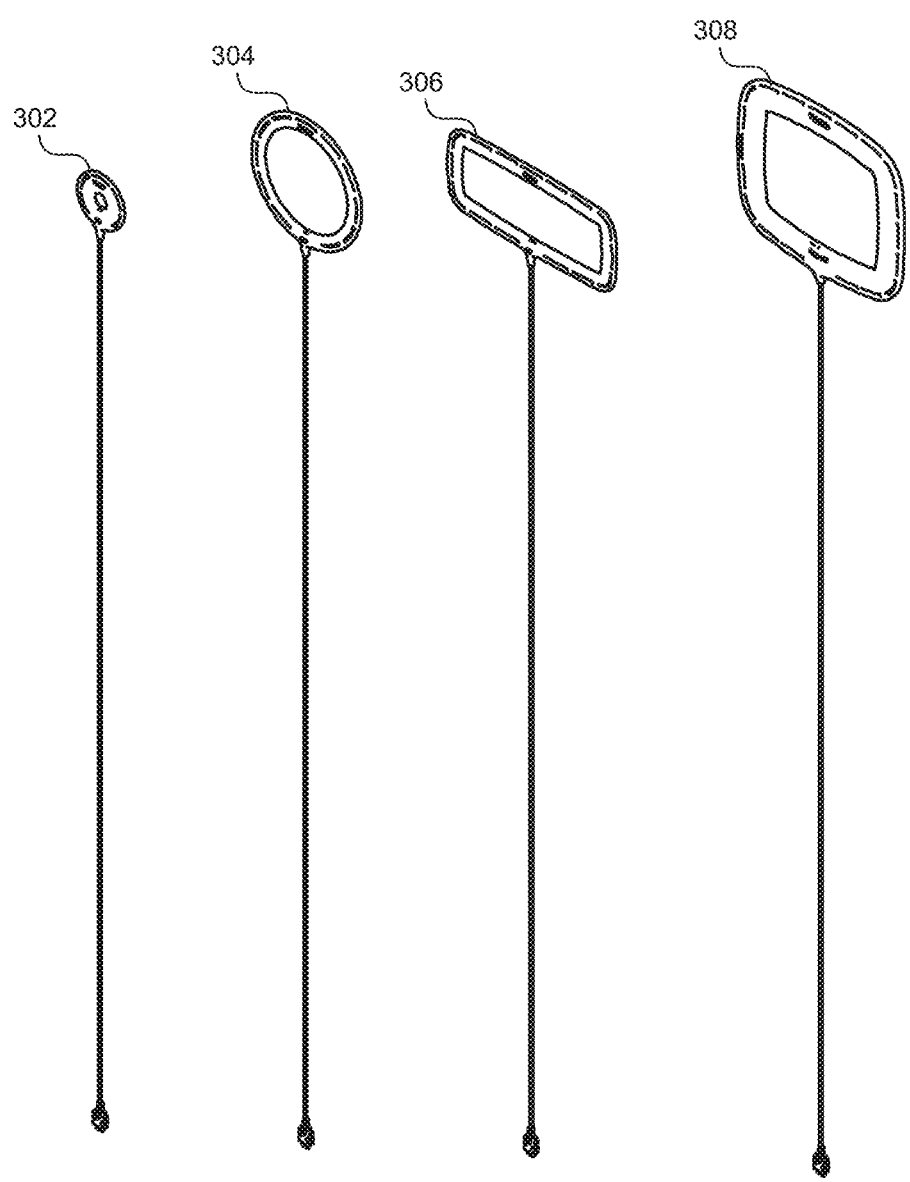
FIG. 3 is a diagram of variations of coils used for providing electromagnetic or magnetic field therapy.

FIG. 3 illustrates diagrams of variations to the shape of the encapsulated coil 202. As illustrated, the coils used by the therapy system 100 may include a small circular encapsulated coil 302, a large circular encapsulated coil 304, a rectangular encapsulated coil 306, and/or a substantially square encapsulated coil 308. Each shape may provide advantages for treating particular parts of the body of the patient.

Figure 4:
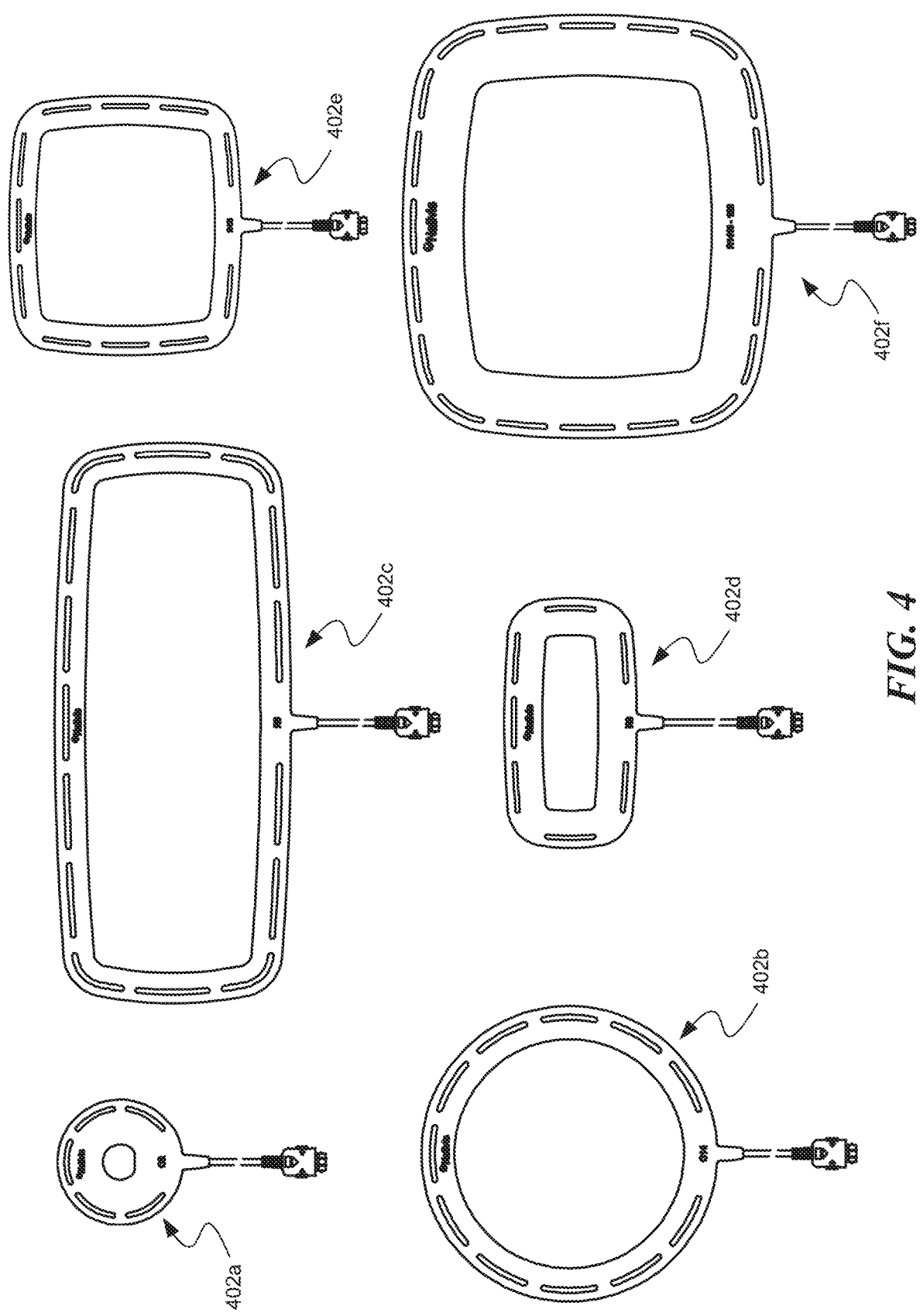
FIG. 4 is a diagram of variations of shapes and sizes of coils used for providing electromagnetic or magnetic field therapy.

FIG. 4 illustrates examples of coils having various shapes and various dimensions. A variety of dimensions for the coils may be manufactured to more effectively apply therapy to areas to be treated that vary in size. Each of the coils 402*a*, 402*b*, 402*c*, 402*d*, 402*d*, 402*f* can have inner and/or outer diameters or lengths, ranging from just a few centimeters to several feet, according to various implementations.

Figure 5B:
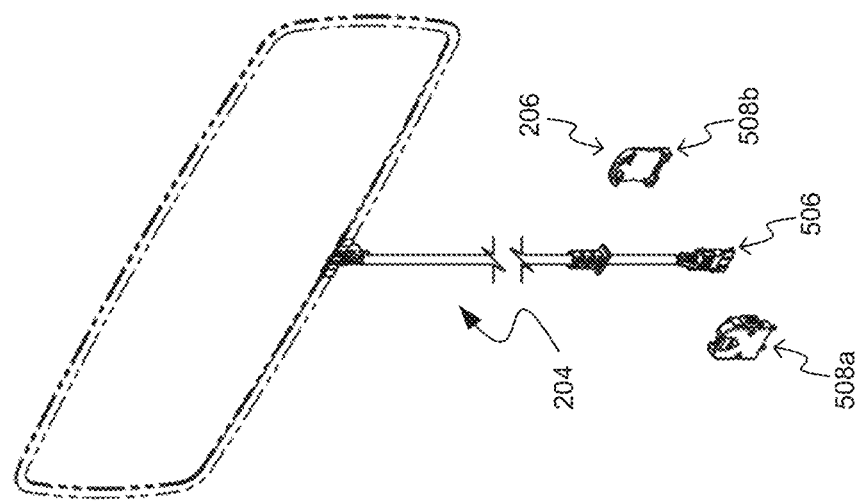
FIGS. 5A-5B are views of the manufacture of a cable for the therapy system.
Figure 5A:
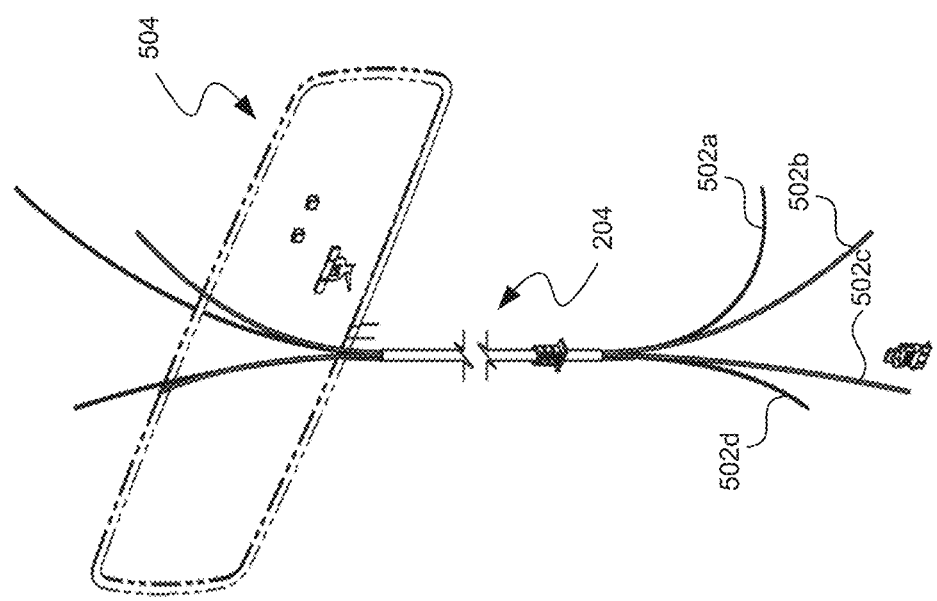

FIGS. 5A and 5B illustrate before and after diagrams of the cable 204 during manufacture. The cable 204 connects a coil, e.g., coil 202, and to the connector 206 to enable the controller 104 to transmit various signals to the coil. The cable 204 may include two or more conductors 502*a*, 502*b*, a shield 502*c*, and a strength-providing member 502*d* (collectively conductors 502). Each of the four conductors and members may be configured to perform a particular function. For example, conductors 502*a* and 502*b* may be electrically coupled to either end of the coil 504 to enable current to flow to and from the coil 504 to activate, stimulate, induce, or otherwise excite the coil 504. Shield conductor 502*c* may be coupled to ground and be configured to provide electromagnetic shielding for the conductors 502*a* and 502*b*. Strength member 502*d* may be anchored to the coil 504 and to the connector 206 to provide strain relief to the conductors 502*a*-502*c*. In some implementations, the strength member 502*d* is manufactured with a shorter length than the other conductors so that the strength member 502*d* receives a majority of any strain applied between the coil 504 and the connector 206.

Figure 6:
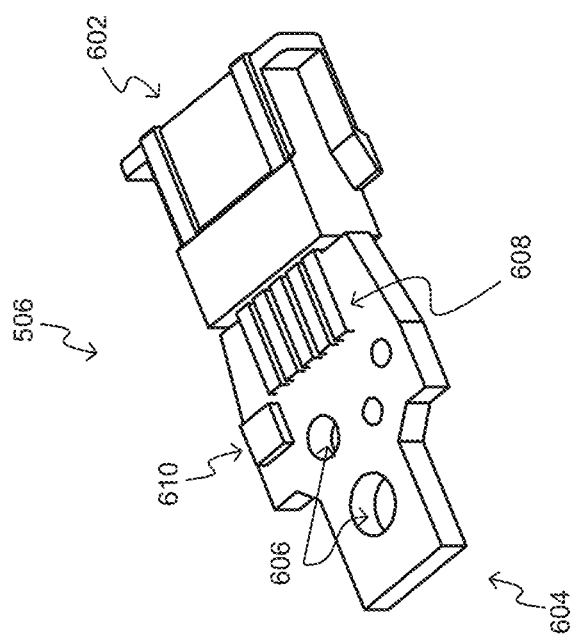
FIG. 6 is a view of a connector for the cable.

As illustrated in FIG. 5B, the connector 206 may include three parts, a connector core 506, and connector housings 508*a* and 508*b*. The connector housings 508*a* and 508*b* may encapsulate the connector core 506 to protect the traces and electronic devices carried by the connector core 506. FIG. 6 illustrates an implementation of the connector core 506. The connector core 506 has a controller end 602 and a cable end 604. The controller end 602 is configured to mateably couple to the controller 104, and the cable end 604 is configured to provide an interface for the conductors 502. In some implementations, the strength member 502*d* may be anchored to one or more holes 606 to provide strain relief. The conductor core 506 may also carry a plurality of traces 608 to which the conductors 502*a*-*c* may be electrically coupled to facilitate communication the controller 104.

As a security feature of the coil and cable assembly 102, the connector core 506 may also carry an integrated circuit 610. The integrated circuit 610 may be a microprocessor or may be a stand-alone memory device. The integrated circuit 610 may be configured to communicate with the controller 104 through the controller end 602 using communication protocols such as I2C, 1-Wire, and the like. The integrated circuit 610 may include a digital identification of the coil with which the connector core 506 is associated. The digital identification stored on the integrated circuit 610 may identify electrical characteristics of the coil, such as impedance, inductance, capacitance, and the like. The integrated circuit 610 may also be configured to store and provide additional information such as the length of the conductor of the coil, physical dimensions of the coil, and number of turns of the coil. In some implementations, the integrated circuit 610 includes information to prevent theft or reuse in a knock-off system, such as a unique identifier, cryptographic data, encrypted information, etc. For example, the information on the integrated circuit 610 may include a cryptographic identifier that represents measurable characteristics of the coil and/or the identification of the integrated circuit. If the cryptographic identifier is merely copied and saved onto another integrated circuit, for example, by an unauthorized manufacturer of the coil and cable assembly, the controller 104 may recognize that the cryptographic identifier is illegitimate and may inhibit signal transmissions. In some implementations, the integrated circuit stores one or more encryption keys, digital signatures, stenographic data or other information to enable communications and/or security features associated with public key infrastructure, digital copy protection schemes, etc.

Figure 7:
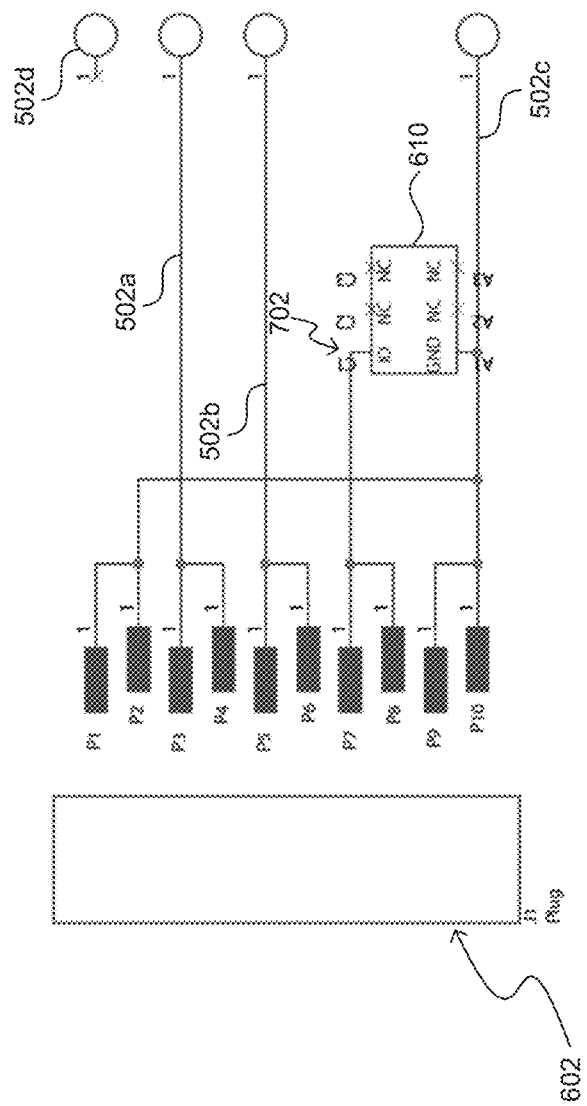
FIG. 7 is a schematic view of the connector for the cable.

FIG. 7 illustrates a schematic diagram of the connector core 506. As shown, according to some implementations, the integrated circuit 610 may be configured to communicate with the controller 104 over a single wire, e.g., from input-output-pin 702.

Figure 8:
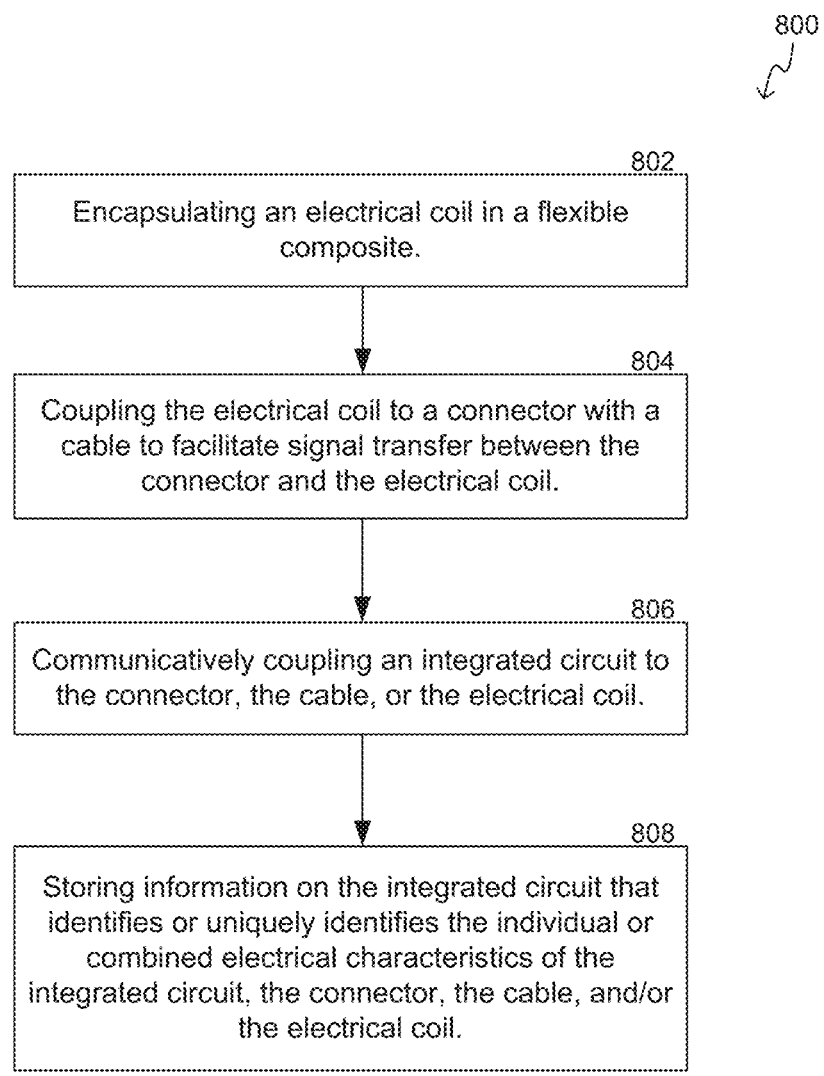
FIG. 8 is a flow diagram of a method of manufacturing a coil for the therapy system.

FIG. 8 illustrates a method 800 of manufacturing a coil and cable assembly, e.g., the coil and cable assembly 102, for use in providing a therapy system that is non-invasive, non-thermal, and mobile.

At block 802, an electrical coil is encapsulated in a flexible composite. The flexible composite allows the electrical coil to be comfortably secured to the body of the patient to provide magnetic field therapy.

At block 804, the electric coil is coupled to a connector through a cable to facilitate secure transfer between the connector and the electrical coil. The cable may include multiple conductors that deliver signals between the connector and the electrical coil while providing mechanical strain relief to the signal carrying conductors.

At block 806, an integrated circuit is coupled to the connector, the cable, or the electrical coil. The integrated circuit may be coupled, for example, to the connector via one or more electrical conductors that may or may not also be coupled to the electrical coil.

At block 808, information is stored to the integrated circuit that identifies or uniquely identifies the individual or combined electrical characteristics of the integrated circuit, the connector, the cable, and/or the electrical coil. The information may be a hash or other cryptographically unique identifier that is based on information that can be unique to the integrated circuit and/or the remainder of the coil and cable assembly. This security feature can be used to prevent or deter unauthorized remanufacture of coil and cable assemblies that are compatible with the controller for the therapy system. Additional security features are described herein, e.g., in connection with the operation of the controller for the therapy system.

Therapy System Controller

Referring briefly back to FIG. 2, the therapy system 100 includes a controller 104 to provide an interface to the patient, to distribute and regulate drug-simulating signals to the coil 202, and to prevent unauthorized copying and/or distribution of the drug-simulating signals. According to various implementations, the controller 104 can include various features such as a housing, a processor, memory, visual and audio interfaces, in addition to other features which are described hereafter in FIGS. 9-15.

Figure 9:
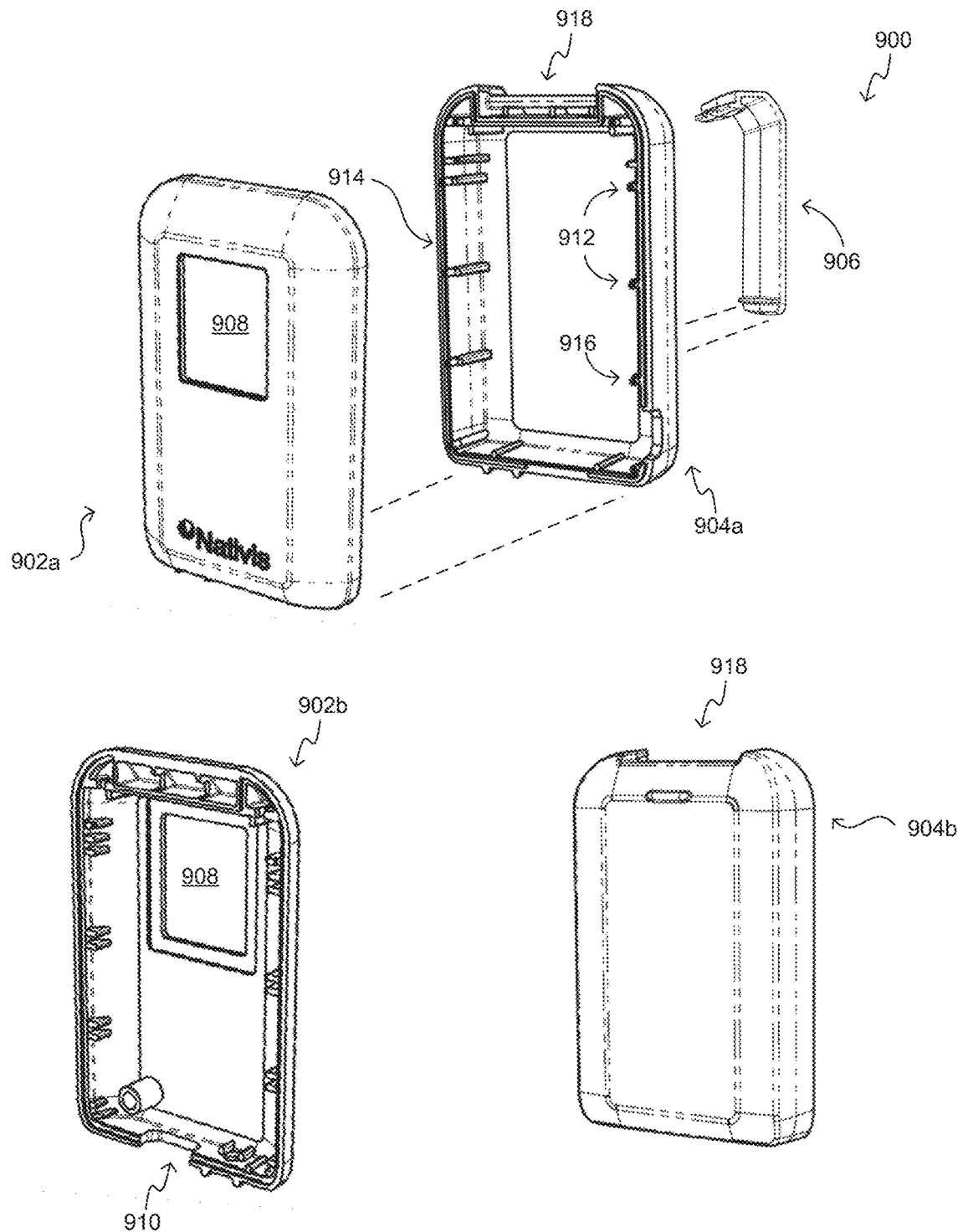
FIG. 9 is an exploded view of a housing of a controller for the therapy system.

FIG. 9 illustrates a housing 900 for the controller 104. The housing 900 may include three parts, a housing front 902 (inclusive of 902a, 902b), a housing back 904 (inclusive of 904a, 904b), and a clip 906. The housing front 902 may have a window 908 through which a visual interface may be viewed or manipulated. Although not shown, the housing front 902 may include various apertures through which buttons, dials, switches, light emitting indicators, and/or a speaker may pass or be disposed. The housing front 902 includes a cut-away or port 910 for coupling the controller 104 to the coil and cable assembly 102. The housing back 904 may include a number of pegs 912 for mateably attaching/securing the housing back 904 to the housing front 902. While coupled together, the housing front 902 and the housing back 904 may form a seal along the edge 914, preventing water, moisture, dust, or other environmental elements from entering the housing 900. In some implementations, an adhesive or solvent is used to permanently bond the housing front 902 to the housing back 904 to deter or prevent unauthorized tampering with or viewing of the internal electronics, though in other implementations the front and back may be formed to permanently snap-fit together. As shown, the housing back 904 may include a cutout, aperture, or port 916 to allow connection to a recharging device or communication information to/from the controller 104. The clip 906 may be securely fastened or detachably coupled to slot 918 of the housing back 904 to secure the controller 104 to the wearer.

FIGS. 10-15 illustrate schematics of electronics that the controller 104 may include to perform the various functions described above. The various electronics may be integrated into one or more programmable controllers or may include discrete electronic components electrically and communicatively coupled to each other.

Figure 10:
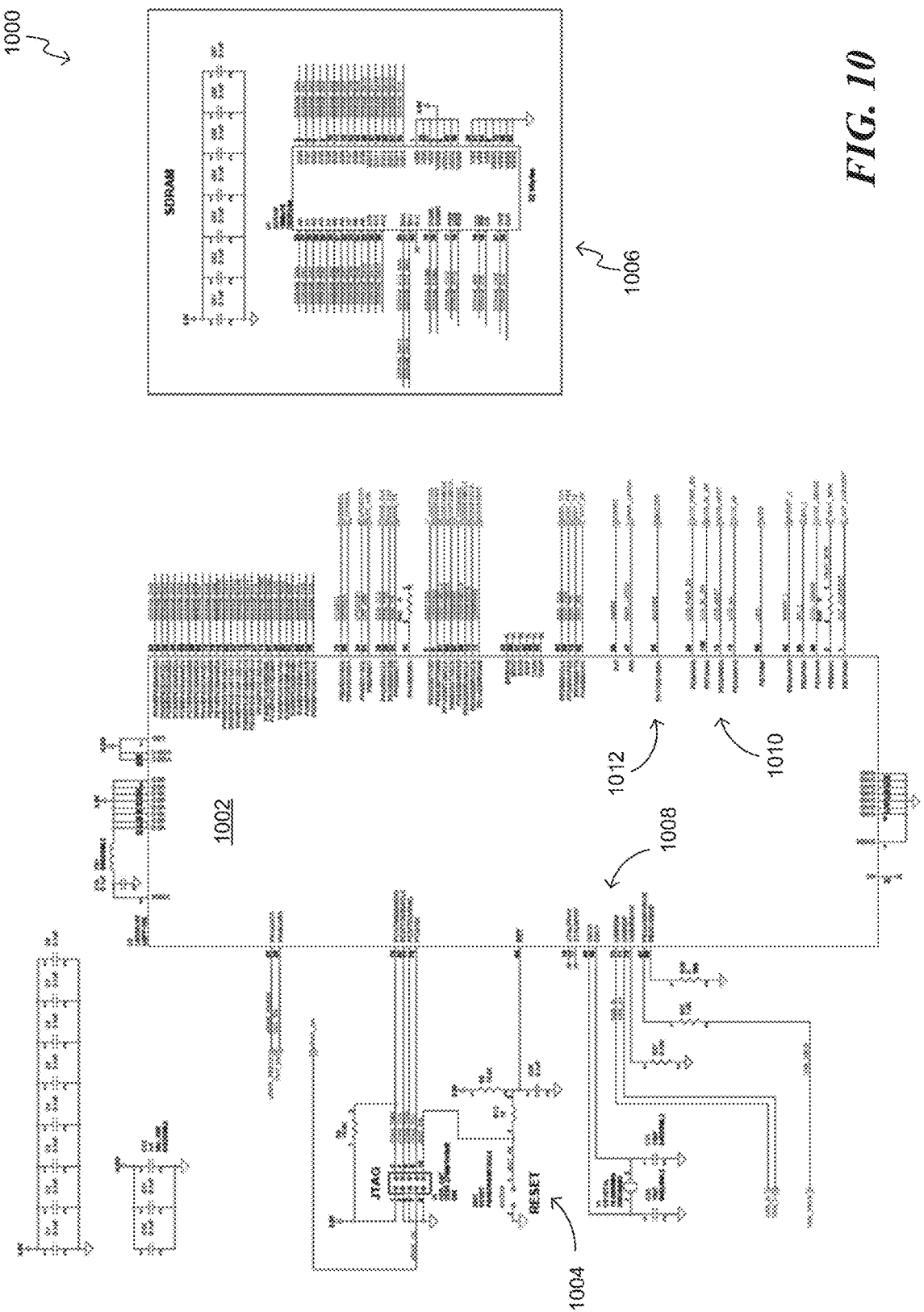
FIG. 10 is an electrical schematic of microprocessor circuitry for the controller.
Figure 11:
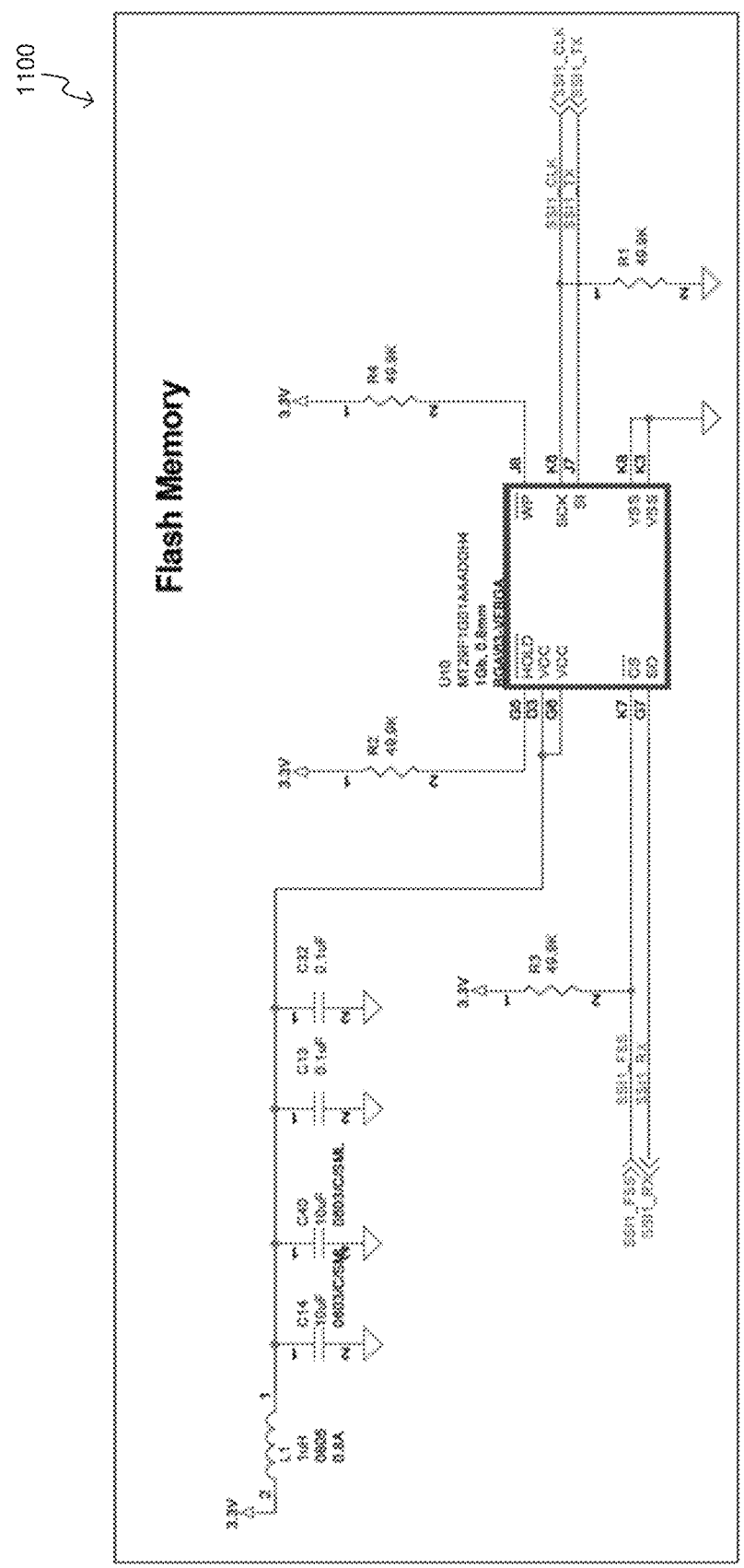
FIG. 11 is an electrical schematic of memory for the controller.

FIG. 10 illustrates microcontroller circuitry 1000 for operating the controller 104. The circuitry 1000 includes a microprocessor 1002, a reset circuit 1004, and a volatile memory 1006. The microcontroller may be a standard microprocessor, microcontroller or other similar processor, or alternatively be a tamper-resistant processor to improve security. The microprocessor 1002 may include a number of analog and/or digital communication pins to support communications with electronics that are both external and internal to the housing 900. The microprocessor 1002 may include USB pins 1008 to support communication via the USB protocol, display pins 1010 to communicate with a visual interface, audio pins 1012 to provide an audio interface, in addition to other data communication pins.

Microcontroller 1002 can be configured to use the USB pins 1008 to securely receive prescription files from one or more external devices. Encryption of the prescription file may increase security of the contents of prescription file. Encryption systems regularly suffer from what is known as the key-distribution-problem. The standard assumption in the cryptographic community is that an attacker will know (or can readily discover) the algorithm for encryption and decryption. The key is all that is needed to decrypt the encrypted file and expose its intellectual property. The legitimate user of the information must have the key. Distribution of the key in a secure way attenuates the key-distribution-problem.

In some embodiments, the microcontroller 1002 is configured to use the Advanced Encryption Standard (AES). AES is a specification for the encryption of electronic data established by the U.S. National Institute of Standards and Technology (NIST) and is used for inter-institutional financial transactions. It is a symmetrical encryption standard (the same key is used for encryption and decryption) and can be secure while the key distribution security is maintained. In some implementations, the microcontroller 1002 uses a 128 bit AES key that is unique to each controller and is stored in non-volatile memory 1100 (illustrated in FIG. 11). The encryption key can be random to reduce the likelihood of forgery, hacking, or reverse engineering. The encryption key can be loaded into non-volatile memory 1100 during the manufacturing process or before the controller is delivered to customers (physicians or patients). Using AES encryption, the prescription file can be encrypted and uploaded to one or more servers to facilitate selective delivery to various controllers 104. For example, a physician or other medical professional may obtain authorization to download prescription files to controllers for his/her patients. When the physician contacts and logs in to a server to obtain a prescription file, the physician may first need to provide certain information, e.g., may need to identify the target device (the controller), for the server (e.g., by a globally unique ID (GUID) stored in the controller) so that the server can look up the target device in a database and provide a prescription file that is encrypted with a key that is compatible with the controller. The encrypted prescription file can then be loaded into the non-volatile memory 1100 via the microcontroller 1002, using USB or another communications protocol. Alternatively or additionally, the encrypted prescription file may be stored directly to the non-volatile memory 1100 during the manufacturing process to reduce the likelihood of interception of the prescription file, and before the front and back portions of the housing are sealed together.

The microcontroller 1002 can also be configured to log use of the therapy system 100 by a patient. The log can be stored in a non-volatile memory 1100 and downloaded by a medical professional when a patient delivers a controller 104 back to the prescribing medical professional, e.g., after the prescribed time allotment for the controller 104 has depleted. The log can be stored in a variety of data formats or files, such as, separated values, as a text file, or as a spreadsheet to enable a medical professional to display activity reports for the controller 104. In some implementations, the microcontroller 1002 is configured to log information related to errors associated with coil connections, electrical characteristics of the coil over time, dates and times of use of the therapy system, battery charge durations and discharge traditions, and inductance measurements or other indications of a coil being placed in contact with a patient's body. The microcontroller 1002 can provide log data or the log file to a medical professional using a USB port or other mode of communication to allow the medical professional to evaluate the quality and/or function of the therapy system and the quantity and/or use of the therapy system by the patient. Notably, the microcontroller 1002 can be configured to log any disruptions in signal delivery and can log any errors, status messages, or other information provided to the user through user interface of the controller 104 (e.g., using the LCD screen).

The microcontroller 1002 can be configured to use the volatile memory 1006 to protect the content of the prescription file. In some implementations, the prescription file is encrypted when the microcontroller 1002 transfers the prescription file from an external source into non-volatile memory 1100. The microcontroller 1002 can then be configured to only store decrypted versions of the content of the prescription file in volatile memory 1006. By limiting the storage of decrypted content to volatile memory 1006, the microcontroller 1002 and thus the controller 104 can ensure that decrypted content is lost when power is removed from the microcontroller circuitry 1000.

The microcontroller 1002 can be configured to execute additional security measures to reduce the likelihood that an unauthorized user will obtain the contents of the prescription file. For example, the microcontroller 1002 can be configured to only decrypt the prescription file after verifying that an authorized or legitimate coil and cable assembly 102 has been connected to the controller 104. As described above, the coil and cable assembly 102 may include an integrated circuit that may store one or more encrypted or not encrypted identifiers for the coil and cable assembly 102. In some implementations, the microcontroller 1002 is configured to verify that an authorized or prescribed coil and cable assembly 102 is connected to the controller 104. The microcontroller 1002 may verify the authenticity of a coil and cable assembly 102 by comparing the identifier from the integrated circuit of the coil and cable assembly 102 with one or more entries stored in a lookup table in either volatile memory 1006 or non-volatile memory 1100. In other implementations, the microcontroller 1002 may be configured to acquire a serial number of the integrated circuit and measure electrical characteristics of the coil and cable assembly 102 and perform a cryptographic function, such as a hash function, on a combination of the serial number and the electrical characteristics. Doing so may deter or prevent an unauthorized user from copying the contents of the integrated circuit of the coil and cable assembly 102 into a duplicate integrated circuit associated with an unauthorized copy of a coil and cable assembly.

The microcontroller 1002 can be configured to delete the prescription file from volatile memory 1006 and from non-volatile memory 1100 in response to fulfillment of one or more predetermined conditions. For example, the microcontroller 1002 can be configured to delete the prescription file from memory after the controller has delivered the prescribed drug-simulating signals for a specific period of time, e.g., 14 days. In other embodiments, the microcontroller 1002 can be configured to delete the prescription file from memory after the controller detects a coupling of the controller 104 with an unauthorized coil and cable assembly. The microcontroller 1002 can be configured to delete the prescriptive file after only one coupling with an unauthorized coil and cable assembly, or can be configured to delete the prescription file after a predetermined number of couplings with an unauthorized coil and cable assembly. In some implementations, the microcontroller can be configured to monitor an internal timer and delete the prescription file, for example, one month, two months, or longer after the prescription file has been installed on the controller 104.

Figure 12:
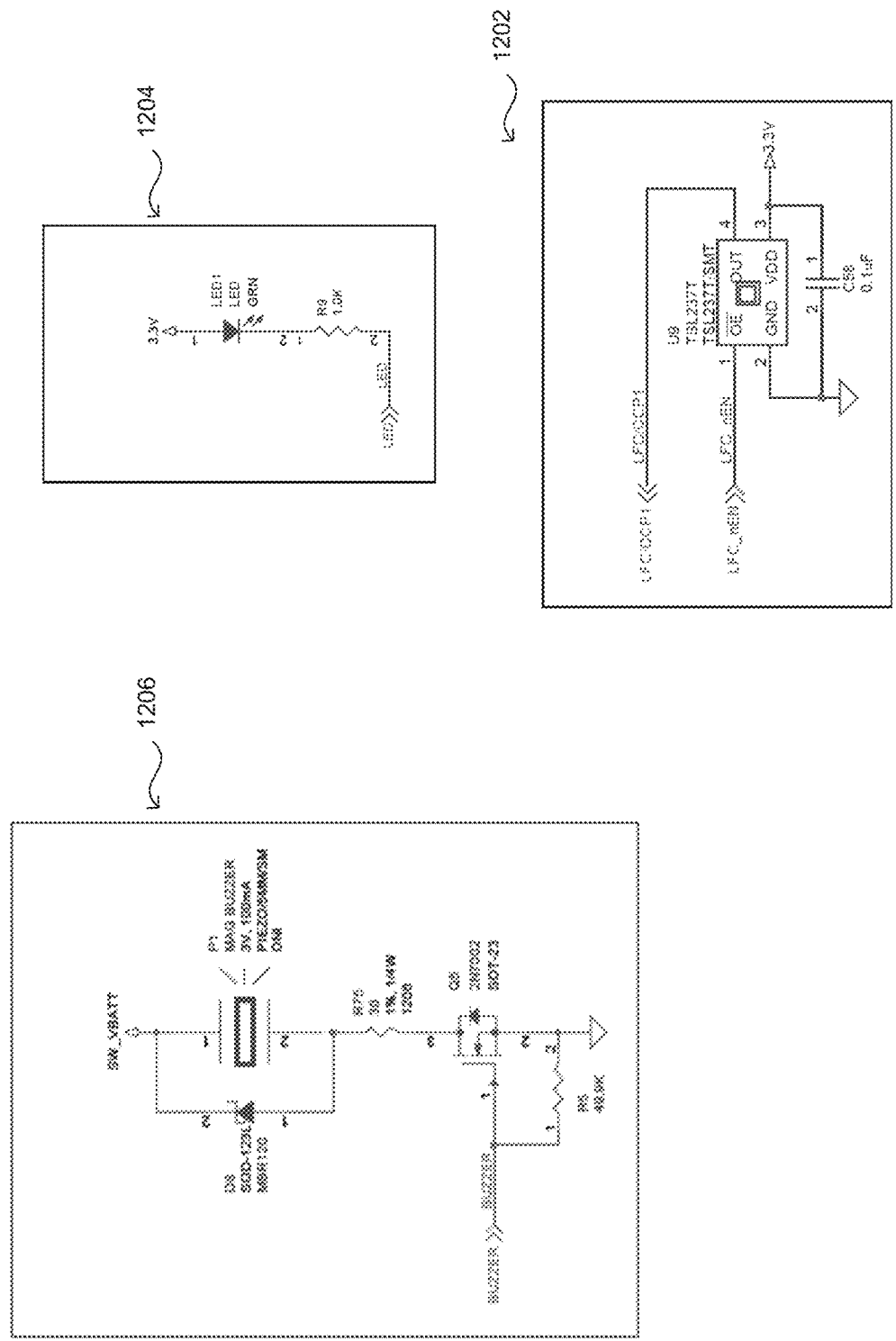
FIG. 12 is an electrical schematic of various components for the controller.

The microcontroller 1002 can be configured to delete the prescription file from volatile memory 1006 and from non-volatile memory 1100 in response to input from one or more sensors. FIG. 12 illustrates a sensor 1202 that may provide a signal to the microcontroller 1002 in response to a physical disruption of the housing 900 of the controller 104. For example, the sensor 1202 can be a light sensor that detects visible and non-visible wavelengths within the electromagnetic spectrum. For example, the sensor 1202 can be configured to detect infrared, visible light, and/or ultraviolet light. Because the detection of light within the housing 900 can be an indication of intrusion into the housing 900, the microcontroller 1002 can be configured to delete and/or corrupt the prescription file upon receipt of a signal from the sensor 1202. In some implementations, the sensor 1202 is a light sensor. In other implementations, the sensor 1202 can be a pressure sensor, a capacitive sensor, a moisture sensor, a temperature sensor, or the like.

In response to detection of unauthorized use of the controller 104, or to increase the user-friendliness of the therapy system 100, the microcontroller 1002 can use various indicators or interfaces to provide information to a user. As examples, FIG. 12 illustrates an LED 1204 and an audible buzzer 1206. The microcontroller 1002 can illuminate the LED 1204 and/or actuate the audible buzzer 1206 in response to user error, unauthorized tampering, or to provide friendly reminders of deviation from scheduled use of the therapy system 100. Although one LED is illustrated in the LED 1204, multiple LEDs having various colors can also be used. Additionally, although the audible buzzer 1206 is described as a buzzer, in other implementations, the audible buzzer 1206 can be a vibrating motor, or a speaker that delivers audible commands to facilitate use of the therapy system 100 by sight impaired professionals and/or patients.

Figure 13:
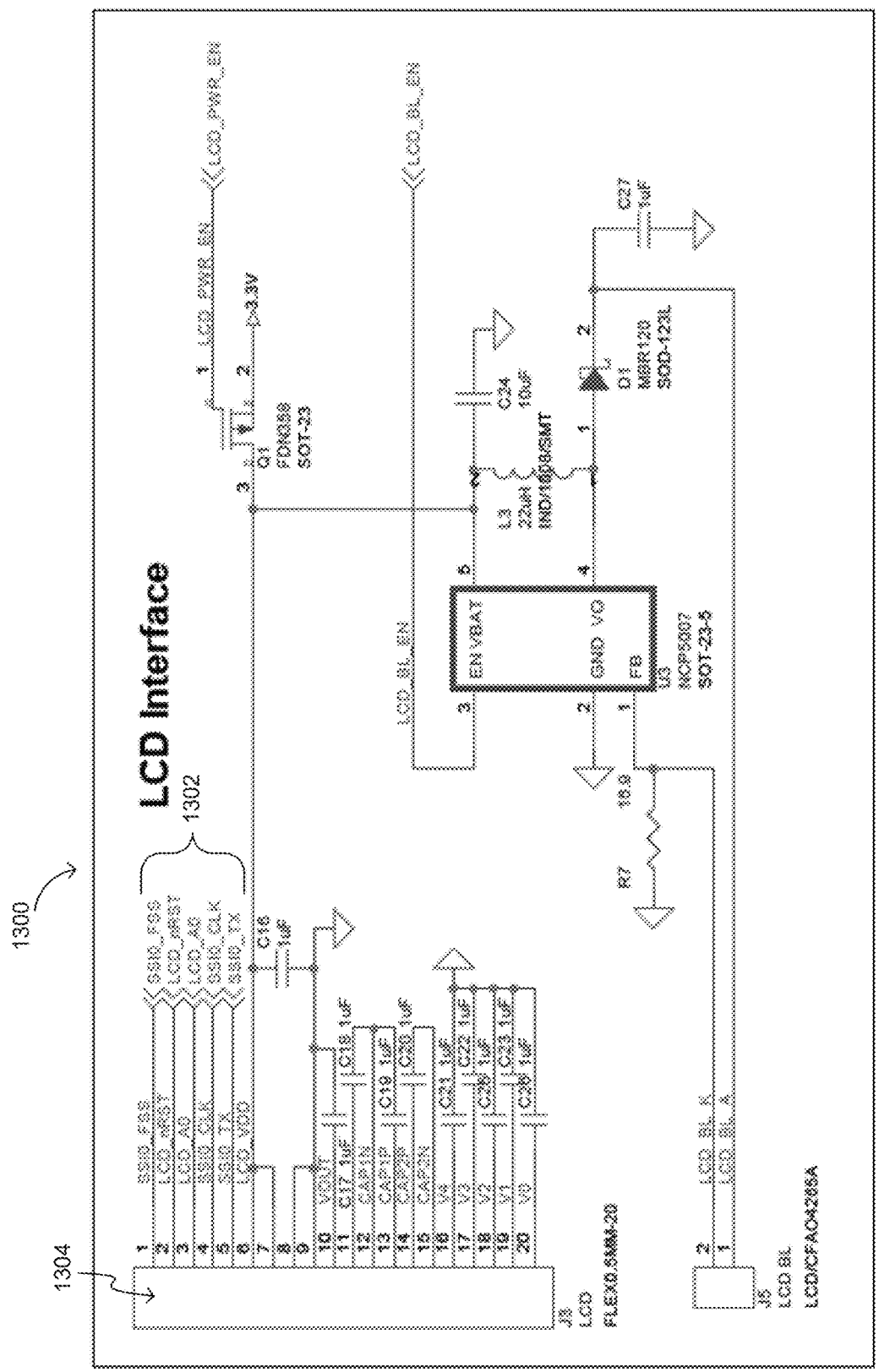
FIG. 13 is an electrical schematic of an LCD interface for the controller.

FIG. 13 illustrates an LCD interface 1300 that the microcontroller 1002 can manipulate to interact with a user. The LCD interface 1300 can receive various commands from the microcontroller 1002 at input pins 1302. In response to inputs received from the microcontroller 1002, an LCD screen 1304 can be configured to display various messages to a user. In some implementations, the LCD screen 1304 displays messages regarding battery status, duration of prescription use, information regarding the type of prescription being administered, error messages, identification of the coil and cable assembly 102, or the like. For example, the LCD screen 1304 can provide a percentage or a time duration of remaining battery power. The LCD screen 1304 can also provide a text-based message that notifies the user that the battery charge is low or that the battery is nearly discharged. The LCD screen 1304 can also be reconfigured to provide a name of a prescription (e.g., corresponding name of the physical drug) and/or a body part for which the prescription is to be used. The LCD screen 1304 can also provide notification of elapsed-time or remaining-time for administration of a prescription. If no additional prescription time is authorized, the LCD screen 1304 can notify the user to contact the user's medical professional.

The LCD screen 1304 can be configured to continuously or periodically provide indications regarding the status of the connection between a coil and the controller. In some implementations, the LCD screen 1304 can be configured to display statuses or instructions such as, "coil connected", "coil not connected", "coil identified", "unrecognized coil", "reconnect coil", or the like. In some implementations, the LCD screen 1304 can provide a graphical representation of a coil and flash the coil when the coil is connected properly or improperly. Alternatively or additionally, the controller can monitor an impedance from the coil to detect a change, a possible removal, or loss of the coil from the area to be treated, and provide a corresponding error message. The LCD interface 1300, in other implementations, can be a touch screen that delivers information to the user in addition to receiving instructions or commands from the user. In some implementations, the microcontroller 1002 can be configured to receive input from hardware buttons and switches to, for example, power on or power off the controller 104. The switch on the device permits an on-off nature of therapy so that patients may selectively switch on and off theft therapy if needed.

Figure 14:
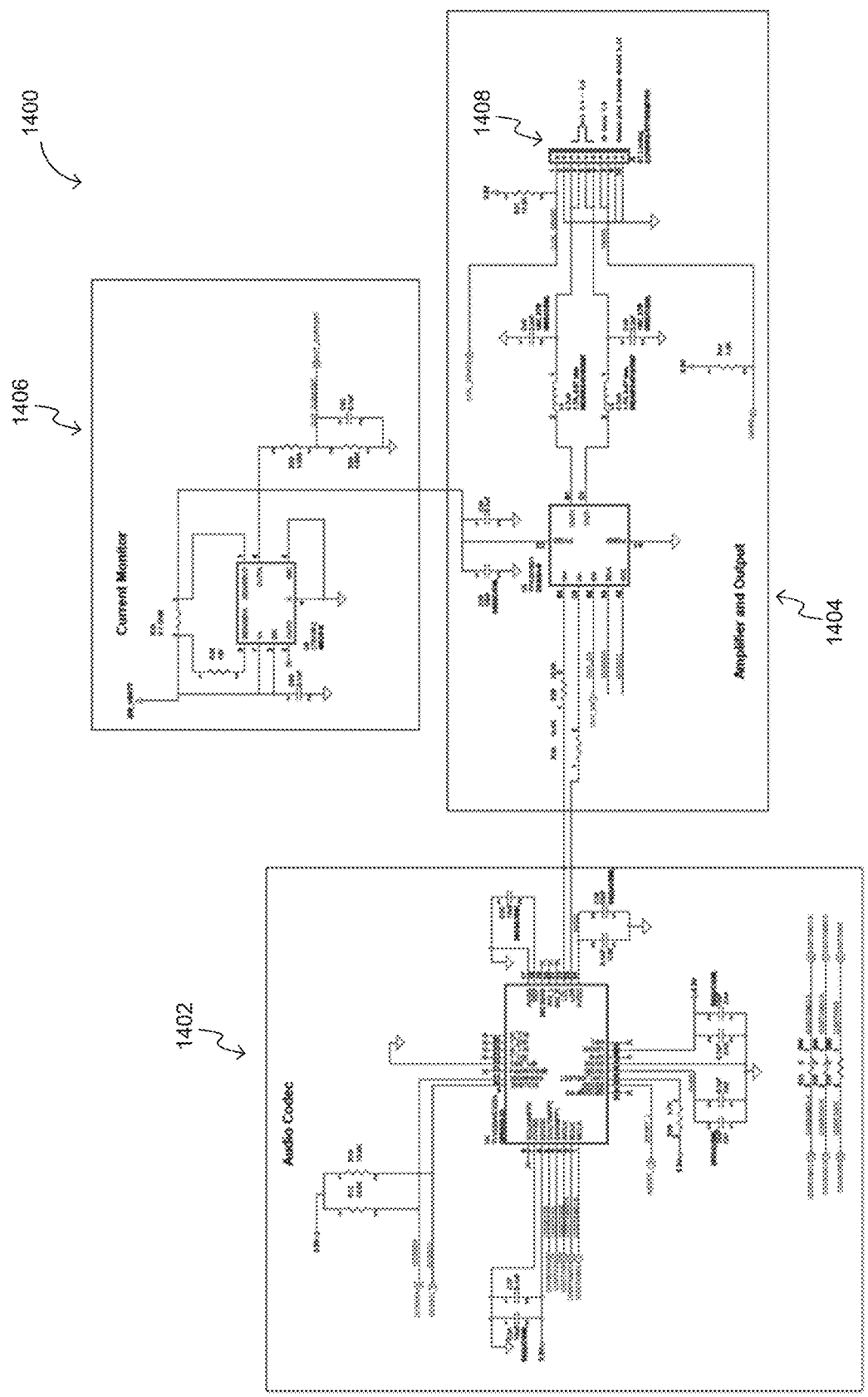
FIG. 14 is an electrical schematic of signal generator circuitry for the controller.

FIG. 14 illustrates signal generation circuitry 1400 that may be used to drive the coil and cable assembly 102 with the drug-simulating signals. The circuitry 1400 may include an audio coder-decoder 1402, and output amplifier 1404, and a current monitor 1406. The audio coder-decoder 1402 may be used to convert digital inputs received from volatile memory 1006, non-volatile memory 1100, or from microcontroller 1002 into analog output signals useful for driving the coil and cable assembly 102. The audio coder-decoder 1402 may be configured to output the analog output signals to the output amplifier 1404. In some implementations, the output amplifier 1404 is programmable so that the intensity or amplitude of the signals transmitted to the coil may be varied according to the treatment prescribed for the patient.

Because the controller 104 can be connected with coils having different sizes, shapes, and numbers of windings, the output amplifier 1404 can be configured to adjust an intensity level of signals delivered to the coil so that each coil delivers a drug-simulating signal that is uniform between different coils, for a particular prescription. The coil dimensions and electrical characteristics can determine the depth and breadth of concentration of the magnetic field, so programmatically adjusting the output intensity of the output amplifier 1404 to deliver uniform drug-simulating signals can advantageously enable a medical professional to select a coil that is appropriate for a particular patient's body or treatment area, without concern for inadvertently altering the prescription. As described above, the controller 104 can determine the dimensions and electrical characteristics of a coil by reading such information from the integrated circuit 610 (shown in FIGS. 6 and 7). The signal generation circuitry 1400 can be configured to use the dimensional and electrical characteristic information acquired from the coil to programmatically adjust the level of intensity of signals output by the output amplifier 1404.

The output amplifier 1404 may include a low pass filter that significantly reduces or eliminates output signals having a frequency higher than, for example, 50 kHz. In other implementations, the low pass filter can be configured to significantly reduce or eliminate output signals having a frequency higher than 25 kHz. The signal generation circuitry 1400 may use the current monitor 1406 to determine electrical characteristics of the coil and cable assembly 102 and/or to verify that output signal levels remain within specified thresholds. The signal generation circuitry 1400 may also include a connector 1408 that mates with the connector 206 of the coil and cable assembly 102. The connector 1408 can provide the electrical interface between the microcontroller 1002 and the coil and cable assembly 102.

In other implementations and as noted above, the signal generation circuitry 1400 can also include inductance detection circuitry. The inductance detection circuitry can be configured to detect changes in the coil inductance. The coil inductance changes when the coil is brought into proximity of a patient's body. By monitoring coil inductance, the signal generation circuitry 1400 and the controller 104 can track and record, i.e., log, a patient's use of the therapy system 100. For example, if a medical professional prescribes 10 hours of use of the therapy system 100, but the controller 104 only logs three hours of use of the therapy system 100, the medical professional may be in a better position to evaluate a patient's improving, non-improving or deteriorating condition. In some implementations, the inductance detection circuitry is implemented as a source follower circuit.

Figure 15:
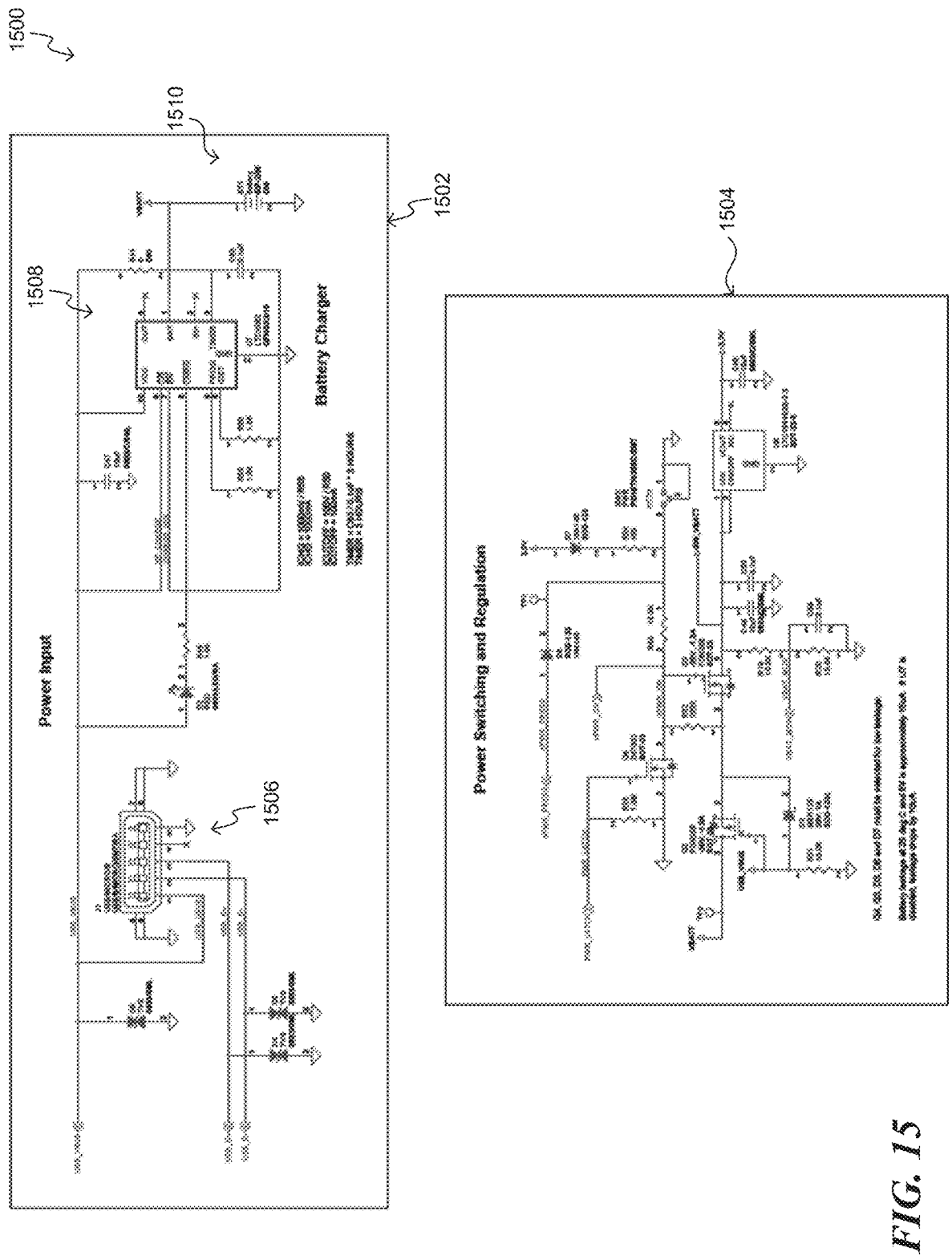
FIG. 15 is an electrical schematic of power regulation circuitry for the controller.

FIG. 15 illustrates power control circuitry 1500 for receiving and regulating power to the controller 104. The power control circuitry 1500 includes power input circuitry 1502 and power regulation circuitry 1504. The power input circuitry 1502 can include a connector 1506, e.g., a micro-USB connector, to receive power from an external source for recharging a battery 1510. The power input circuitry 1502 can also include a charging circuit 1508 that monitors a voltage level of the battery 1510 and electrically decouples the battery from the connector 1506 when the battery 1510 is sufficiently charged. The power regulation circuitry 1504 can be used to convert a voltage level of the battery 1510 to a lower voltage for use by the various circuits of the controller 102. For example, when fully charged, the battery 1510 may have a voltage of about 4.2 to 5 volts, whereas the microcontroller may have an upper voltage threshold of 3.5 volts. The power regulation circuitry 1504 can be configured to convert the higher voltage of the battery, e.g., 4.2 volts, to a lower voltage, e.g., 3.3 volts, that is usable by the electronic devices of the controller 102.

Figure 16:
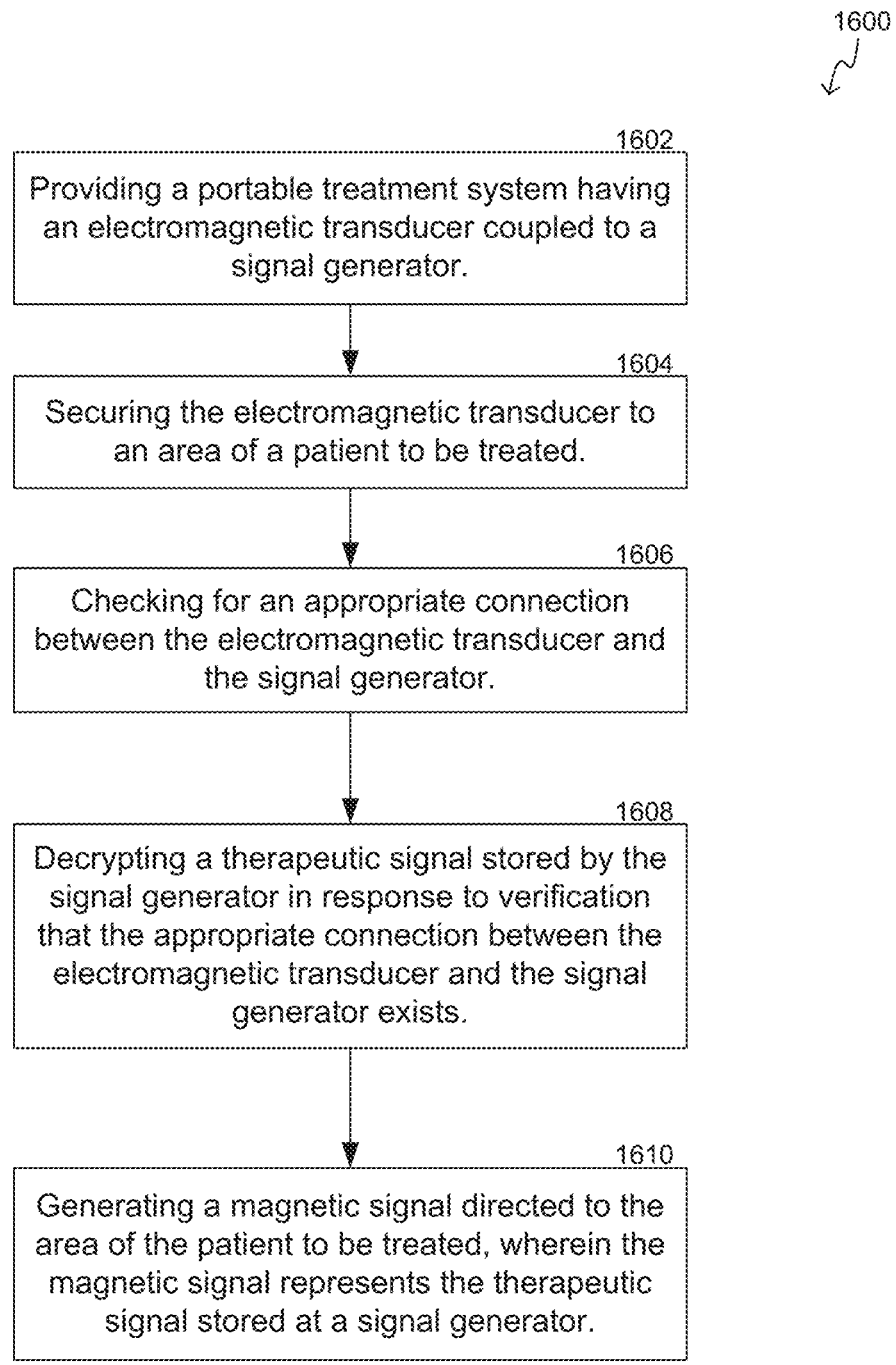
FIG. 16 is flow diagram of a method of operating the therapy system.

FIG. 16 illustrates a method 1600 of operating a portable therapy system that may be used to provide magnetic field therapy that is non-invasive, non-thermal, and mobile.

At block 1602 an electromagnetic transducer is coupled to a signal generator. The electromagnetic transducer can be a coil having various shapes and sizes according to the size or condition of an ailment to be treated.

At block 1604 the electromagnetic transducer is secured to an area of the patient to be treated. The transducer may be secured using elastic bandages, gauze, tape, or the like.

At block 1606, the signal generator checks for an appropriate connection to the electromagnetic transducer. The signal generator can be configured to verify an identification or electrical characteristics of the electromagnetic transducer, such as a resistance or impedance of the transducer to ensure that an appropriate transducer is coupled to the generator. In some implementations, the signal generator can be configured to periodically monitor the electrical characteristics of the electromagnetic transducer to ensure that an appropriate connection is maintained. For example, if the signal generator detects an increase in resistance or decrease in inductance, the signal generator may be configured to cease delivery of signals to the electromagnetic transducer. The signal generator may cease delivery of signals when unexpected electrical characteristics are detected to protect the health and safety of the patient and to prevent unauthorized attempts to acquire generated signals. As discussed above, the signal generator may be configured to log the periodic checks of the electrical characteristics of the electromagnetic transducer and can provide the log data to a medical professional for review. Other security checks may be performed as described herein.

At block 1608 the signal generator decrypts a therapeutic signal stored by the signal generator in response to verification that an appropriate connection between the electromagnetic transducer and the signal generator exists.

At block 1610 the electromagnetic transducer generates a magnetic signal directed to an area of the patient to be treated. The magnetic signal is representative of the therapeutic signal stored at the signal generator. According to various implementations, the magnetic signal has a frequency in the range of 1 Hz to 22 kHz.

In some implementations, a signal from a sample of a drug, biologic, or molecule (chemical, biochemical, biological), may be acquired by placing a sample in an electromagnetic shielding structure and by placing the sample proximate to at least one superconducting quantum interference device (SQUID) or magnetometer. The drug sample is placed in a container having both magnetic and electromagnetic shielding, where the drug sample acts as a signal source for molecular signals. Noise is injected into the drug sample in the absence of another signal from another signal source at a noise amplitude sufficient to generate stochastic resonance, where the noise has a substantially uniform amplitude over multiple frequencies. Using the superconducting quantum interference device (SQUID) or the magnetometer, output radiation from the drug sample is detected and recorded as an electromagnetic time-domain signal composed of drug sample-source radiation superimposed on the injected noise in the absence of the another generated signal. The injecting of noise and detecting of the radiation may be repeated at each of multiple noise levels within a selected noise-level range until the drug sample source radiation is distinguishable over the injected noise.

Figure 17B:
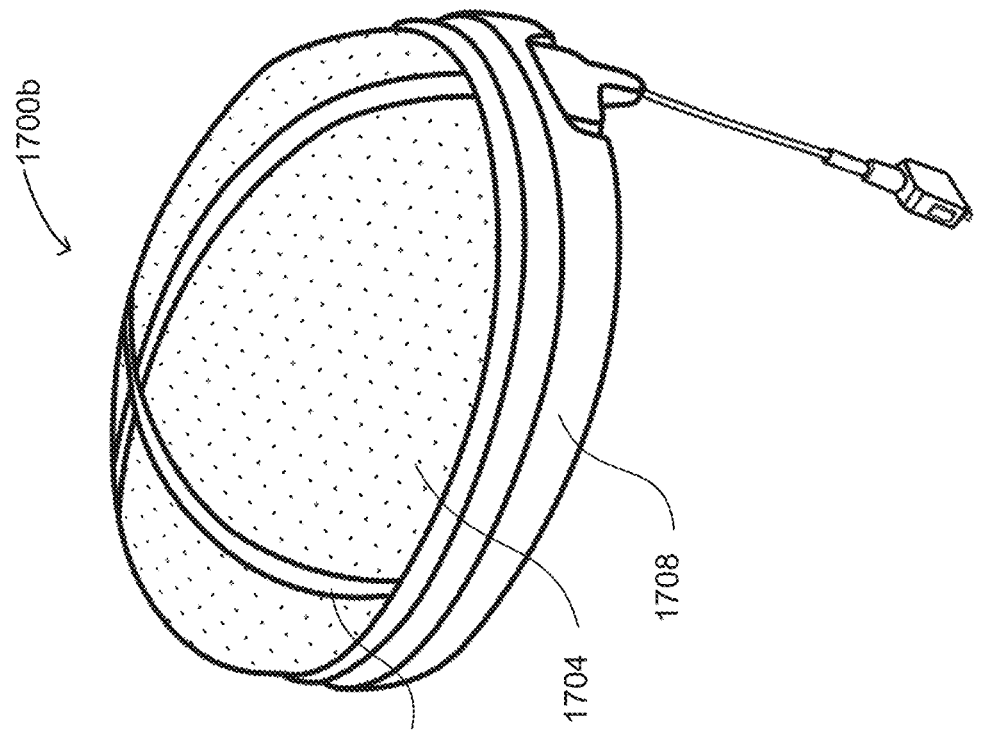
FIGS. 17A-17B show diagrams of an example apparatus for securing the therapy system to the cranium of a human patient.
Figure 17A:
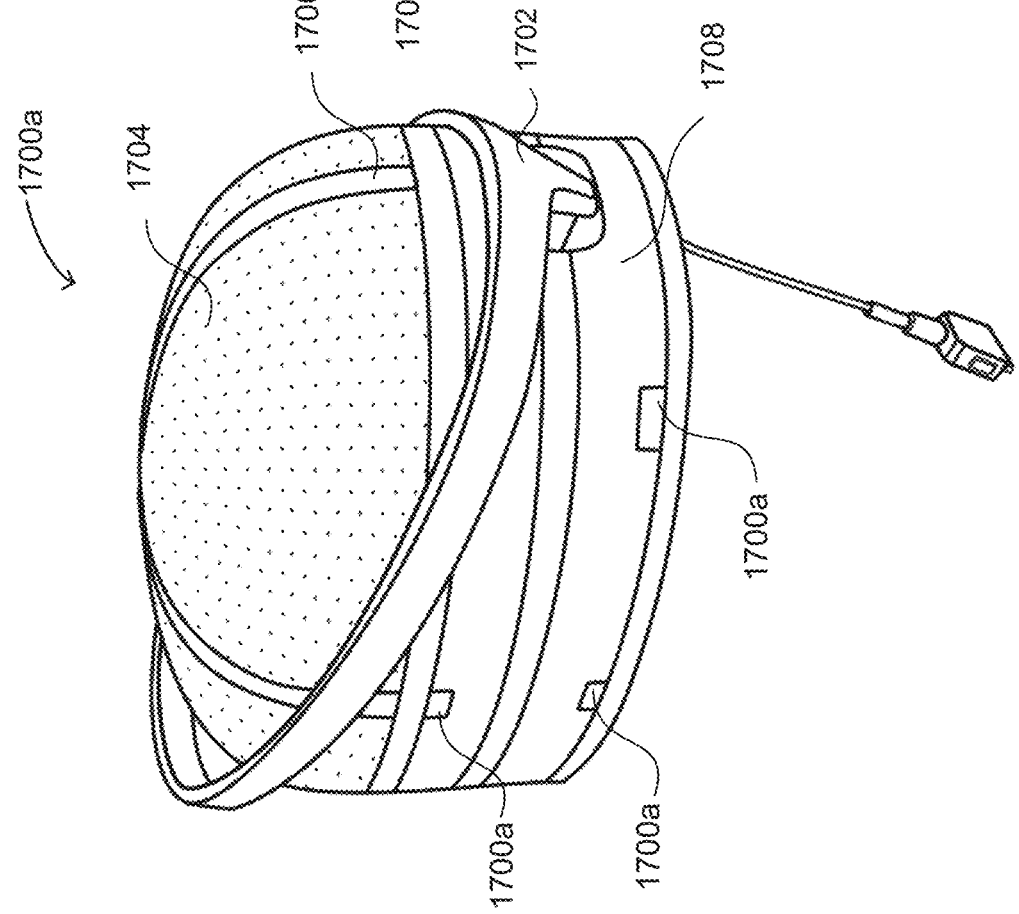

FIGS. 17A and 17B illustrate example embodiments of headgear 1700 (inclusive of 1700*a* and 1700*b*) that may be used to position or secure a coil 1702 around the cranium of a human patient. The headgear can include a breathable mesh 1704, elastic straps 1706, and a band 1708. The breathable mesh 1704, elastic straps 1706, and the band 1708 can provide a comfortable apparatus for carrying, securing, or otherwise positioning the coil 1702 around the cranium of a patient. The headgear 1700 may also include fasteners 1710 (inclusive of 1710*a*, 1710*b*, 1710*c*) for securing the band 1708 over the coil 1702. The fasteners 1710 may be influenced with Velcro, snaps, or other types of securing devices. In FIG. 17A, the headgear 1700*a* illustrates the coil 1702 in an exposed or unsecured position. In FIG. 17B, the headgear 1700*b* illustrates the coil 1702 in a secured position.

Figure 18:
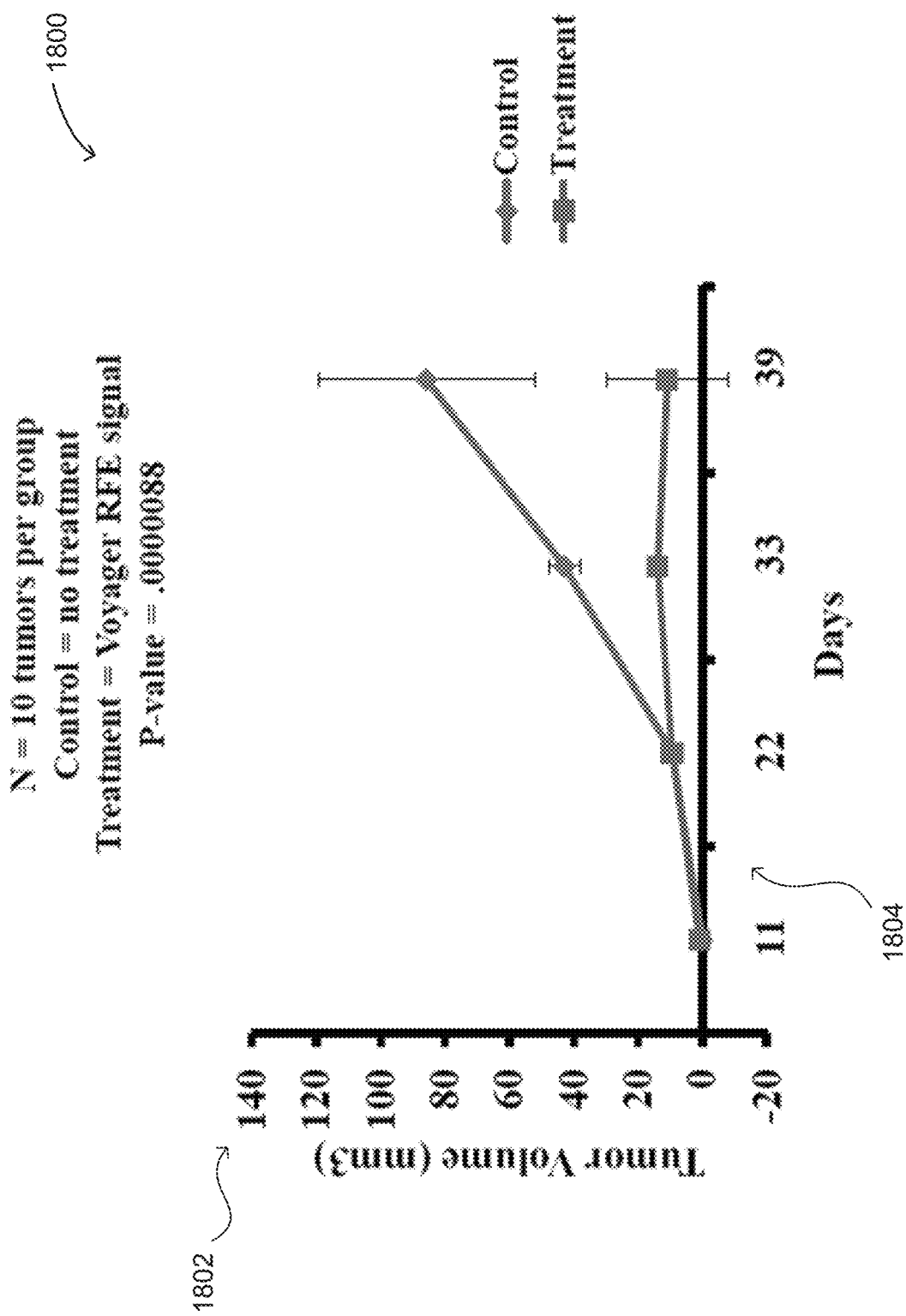
FIG. 18 is a chart comparing U87 glioblastoma multiforme human cell line solid tumor volume of control mouse subjects to treated mouse subjects in a mouse study model.

FIG. 18 is a chart 1800 comparing tumor volume of control mouse subjects to treated mouse subjects in a mouse study model. In the study, 10 tumors, U87 glioblastoma multiforme human cell line solid tumors in mice, were monitored in each of the control group and the treated group. As part of the study, no treatment was administered to the control group, and a system similar to the therapy system 100 delivered drug-simulating signals or radio frequency energy signals to the treatment group. The chart 1800 includes a y-axis 1802 that displays tumor volume in cubic millimeters. The chart 1800 also includes an x-axis 1804 that displays elapsed time on a scale of days. As shown in the mouse study, a possibility exists that administration of particular drug-simulating signals may maintain or reduce a volume of malignant growths or tumors over an extended period of time.

Definitions

The terms below generally have the following definitions unless indicated otherwise. Such definitions, although brief, will help those skilled in the relevant art to more fully appreciate aspects of the invention based on the detailed description provided herein. Other definitions are provided above. Such definitions are further defined by the description of the invention as a whole (including the claims) and not simply by such definitions.

"Radio frequency energy" refers to magnetic fields having frequencies in the range of approximately 1 Hz to 22 kHz.

"Magnetic shielding" refers to shielding that decreases, inhibits or prevents passage of magnetic flux as a result of the magnetic permeability of the shielding material.

"Electromagnetic shielding" refers to, e.g., standard Faraday electromagnetic shielding, or other methods to reduce passage of electromagnetic radiation.

"Faraday cage" refers to an electromagnetic shielding configuration that provides an electrical path to ground for unwanted electromagnetic radiation, thereby quieting an electromagnetic environment.

"Time-domain signal" or 'time-series signal" refers to a signal with transient signal properties that change over time.

"Sample-source radiation" refers to magnetic flux or electromagnetic flux emissions resulting from molecular motion of a sample, such as the rotation of a molecular dipole in a magnetic field. Because sample source radiation may be produced in the presence of an injected magnetic-field stimulus, it may also be referred to as "sample source radiation superimposed on injected magnetic field stimulus."

"Stimulus magnetic field" or "magnetic-field stimulus" refers to a magnetic field produced by injecting (applying) to magnetic coils surrounding a sample, one of a number of electromagnetic signals that may include (i) white noise, injected at voltage level calculated to produce a selected magnetic field at the sample of between 0 and 1 G (Gauss), (ii) a DC offset, injected at voltage level calculated to produce a selected magnetic field at the sample of between 0 and 1 G, and/or (iii) sweeps over a low-frequency range, injected successively over a sweep range between at least about 0-1 kHz, and at an injected voltage calculated to produce a selected magnetic field at the sample of between 0 and 1 G. The magnetic field produced at the sample may be readily calculated using known electromagnetic relationships, knowing a shape and number of windings in an injection coil, a voltage applied to coils, and a distance between the injection coils and the sample.

A "selected stimulus magnetic-field condition" refers to a selected voltage applied to a white noise or DC offset signal, or a selected sweep range, sweep frequency and voltage of an applied sweep stimulus magnetic field.

"White noise" refers to random noise or a signal having simultaneous multiple frequencies, e.g., white random noise or deterministic noise. Several variations of white noise and other noise may be utilized. For example, "Gaussian white noise" is white noise having a Gaussian power distribution. "Stationary Gaussian white noise" is random Gaussian white noise that has no predictable future components. "Structured noise" is white noise that may contain a logarithmic characteristic which shifts energy from one region of the spectrum to another, or it may be designed to provide a random time element while the amplitude remains constant. These two represent pink and uniform noise, as compared to truly random noise which has no predictable future component. "Uniform noise" means white noise having a rectangular distribution rather than a Gaussian distribution.

"Frequency-domain spectrum" refers to a Fourier frequency plot of a time-domain signal.

"Spectral components" refers to singular or repeating qualities within a time-domain signal that can be measured in the frequency, amplitude, and/or phase domains. Spectral components will typically refer to signals present in the frequency domain.

Conclusion

The system described herein transduces a specific molecule signal to effect a specific charge pathway and may be configured to deliver the effect of chemical, biochemical or biologic therapy to a patient and treat an adverse health condition, without the use of drugs, alternative therapies, etc. For example, the system can transduce RNA sequence signals to regulate metabolic pathways and protein production, both up regulation and down regulation.

The system provides numerous other benefits. The system is scalable to provide treatment to a variety of patient regions. The coil, cable and connector are disposable, or the device as a whole with the controller, are preferably provided for a single therapeutic session and for one prescription, so that the device and coil are not to be reused, thereby preventing cross contamination, etc. The switch on the device permits an on-off nature of therapy so that patients may selectively switch on and off their therapy if needed.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

The teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the signal processing system may vary considerably in its implementation details, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

We claim:

1. An apparatus for generating a therapeutic electromagnetic field signal to provide treatment for one or more ailments, the apparatus comprising:
   an electromagnetic transducer having a terminal and a signal output portion coupled to a connector; and,
   a signal generator comprising—
      at least one processor coupled to the terminal;
      a computer-readable medium, excluding transitory signals, coupled to the at least one processor and storing a therapeutic signal obtained from a sample of a chemical or biologic molecule including proteins, RNA and DNA sequences and storing processorexecutable instructions that, when executed by the at least one processor, cause the at least one processor to:
produce, through the electromagnetic transducer, the therapeutic electromagnetic field signal in response to the stored therapeutic signal to provide treatment for the one or more ailments, and
start a timer and, when the timer reaches a predetermined value, disable the signal generator of the apparatus to prohibit reuse of the stored therapeutic signal,
wherein the therapeutic electromagnetic field signal is produced at a location proximate to the signal output portion of the electromagnetic transducer and has a frequency in a frequency range between 1 Hz to 22 kHz; and
wherein disabling the signal generator includes erasing the stored therapeutic signal;
a battery coupled at least to the at least one processor; and
a housing for carrying the computer-readable medium, the at least one processor, and the battery
wherein the processor is programmed to provide the stored therapeutic signal for delivery to the electromagnetic transducer.

2. The apparatus of claim 1, wherein the therapeutic electromagnetic field signal is produced from a frequency-domain spectrum produced from a time-domain or time-series signal with transient properties that change over time.

3. The apparatus of claim 1, wherein the instructions further cause the at least one processor to unsecure or decrypt the stored therapeutic signal.

4. The apparatus of claim 3, wherein the stored therapeutic signal is encrypted within the signal generator, and wherein unsecuring the stored therapeutic signal includes decrypting the stored therapeutic signal.

5. The apparatus of claim 1, wherein the instructions further cause the at least one processor to check for an appropriate connection between the electromagnetic transducer and the signal generator portion.

6. The apparatus of claim 5, wherein checking for the appropriate connection includes determining a type of the electromagnetic transducer.

7. The apparatus of claim 6, wherein the instructions further cause the at least one processor to adjust an amplification of the therapeutic electromagnetic field signal based on the determined type.

8. The apparatus of claim 5, wherein checking for the appropriate connection includes reading identification information from the electromagnetic transducer.

9. The apparatus of claim 5, wherein checking for the appropriate connection includes periodically confirming that the electromagnetic transducer continues to maintain a physical resistance value within tolerance.

10. The apparatus of claim 1, wherein the therapeutic signal is obtained from the sample by:
providing the sample of the chemical or biologic molecule including proteins, RNA and DNA sequences within an electromagnetic shielding structure and proximate to at least one superconducting quantum interference device (SQUID) or magnetometer;
placing the sample in a container having both magnetic and electromagnetic shielding,
wherein the sample acts as a signal source for the therapeutic signal;
injecting noise into the sample in the absence of another signal from another signal source at a noise amplitude sufficient to generate stochastic resonance,
wherein the noise has a substantially uniform amplitude over multiple frequencies;
detecting, via the SQUID or magnetometer, output radiation from the sample and recording an electromagnetic time-domain signal composed of sample source radiation superimposed on the injected noise in the absence of the another signal; and
repeating the injecting and detecting at each of multiple noise levels within a selected noise-level range until source radiation from the sample is distinguishable over the injected noise.

11. A system for generating therapeutic electromagnetic field signals to provide treatment for one or more ailments, the system comprising:
one or more processors each coupled to one or more batteries;
a plug;
a therapeutic device having
a connector,
a housing,
a port to receive the plug, and
an electromagnetic transducer portion including
a terminal, and
a signal output portion coupled to the connector; and
one or more memories, coupled to the one or more processors and storing a therapeutic signal and storing instructions that, when executed by the one or more processors,
cause the system to:
direct the electromagnetic transducer portion to produce a therapeutic electromagnetic field signal in response to the therapeutic signal, and
cause the one or more processors to:
adjust an amplification of the therapeutic electromagnetic field signal based on a determined type of the therapeutic device,
wherein the stored therapeutic signal is obtained from a sample of a chemical or biologic molecule including proteins, RNA and DNA sequences to provide treatment for ailments at a location proximate to the signal output portion,
wherein the therapeutic electromagnetic field signal has a frequency in a frequency range between 1 Hz to 22 kHz, and
wherein the therapeutic electromagnetic field signal is produced from a frequency-domain spectrum produced from a time-domain or time-series signal that changes over time.

12. The system of claim 11, wherein the therapeutic electromagnetic field signal is secured or encrypted, and wherein the instructions further cause the one or more processors to unsecure or decrypt the therapeutic electromagnetic field signal.

13. The system of claim 11, wherein the therapeutic signal is obtained from the sample by:
providing the sample of the chemical or biologic molecule including proteins, RNA and DNA sequences within an electromagnetic shielding structure and proximate to at least one superconducting quantum interference device (SQUID) or magnetometer;
placing the sample in a container having both magnetic and electromagnetic shielding,
wherein the sample acts as a signal source for the therapeutic signal;

injecting noise into the sample in the absence of another signal from another signal source at a noise amplitude sufficient to generate stochastic resonance,
wherein the noise has a substantially uniform amplitude over multiple frequencies;

detecting, via the SQUID or magnetometer, output radiation from the sample and recording an electromagnetic time-domain signal composed of sample source radiation superimposed on the injected noise in the absence of the another signal; and repeating the injecting and detecting at each of multiple noise levels within a selected noise-level range until source radiation from the sample is distinguishable over the injected noise.

14. An apparatus for generating therapeutic electromagnetic field signals from at least one stored therapeutic signal that treat one or more ailments in a subject, the apparatus comprising:
an electromagnetic transducer having a terminal and a signal output portion coupled to a connector; and,
a signal generator comprising—
a computer-readable medium, excluding transitory signals, for storing the at least one therapeutic signal and carrying instructions that, when executed by at least one processor coupled to the computer-readable medium and the terminal, cause the at least one processor to:
direct the electromagnetic transducer to produce a therapeutic electromagnetic field signal based upon the at least one stored therapeutic signal obtained from a sample of a chemical or biologic molecule including proteins, RNA and DNA sequences at a location of the subject proximate to the signal output portion, and
adjust an amplification of the therapeutic electromagnetic field signal based on a determined type of the therapeutic device,
wherein the therapeutic electromagnetic field signal has a frequency in a frequency range between 1 Hz to 22 kHz;
a battery coupled at least to the at least one processor; and
a housing for carrying the computer-readable medium, the at least one processor, and the battery.

15. The system of claim 14, wherein the therapeutic electromagnetic field signal is secured or encrypted, and wherein the instructions further cause the processor to unsecure or decrypt the therapeutic electromagnetic field signal.

16. The apparatus of claim 14, wherein the therapeutic electromagnetic field signal is produced from a frequency-domain spectrum produced from a time-domain or time-series signal that changes over time.

17. The system of claim 14, wherein the at least one therapeutic signal is obtained from the sample by:
providing the sample of the chemical or biologic molecule including proteins, RNA and DNA sequences within an electromagnetic shielding structure and proximate to at least one superconducting quantum interference device (SQUID) or magnetometer;
placing the sample in a container having both magnetic and electromagnetic shielding,
wherein the sample acts as a signal source for the at least one therapeutic signal;
injecting noise into the sample in the absence of another signal from another signal source at a noise amplitude sufficient to generate stochastic resonance,
wherein the noise has a substantially uniform amplitude over multiple frequencies;
detecting, via the SQUID or magnetometer, output radiation from the sample and recording an electromagnetic time-domain signal composed of sample source radiation superimposed on the injected noise in the absence of the another signal; and
repeating the injecting and detecting at each of multiple noise levels within a selected noise-level range until source radiation from the sample is distinguishable over the injected noise.

* * * * *